US006919046B2

(12) United States Patent
O'Connor et al.

(10) Patent No.: US 6,919,046 B2
(45) Date of Patent: Jul. 19, 2005

(54) MICROFLUIDIC ANALYTICAL DEVICES AND METHODS

(75) Inventors: Stephen D. O'Connor, Pasadena, CA (US); Christoph D. Karp, Pasadena, CA (US); Marci Pezzuto, Altadena, CA (US); Courtney Coyne, Pasadena, CA (US); Steven E. Hobbs, West Hills, CA (US); Eugene Dantsker, Sierra Madre, CA (US)

(73) Assignee: Nanostream, Inc., Pasadena, CA (US)

( * ) Notice: Subject to any disclaimer, the term of this patent is extended or adjusted under 35 U.S.C. 154(b) by 596 days.

(21) Appl. No.: 10/164,887

(22) Filed: Jun. 7, 2002

(65) Prior Publication Data

US 2002/0187074 A1 Dec. 12, 2002

Related U.S. Application Data

(60) Provisional application No. 60/296,897, filed on Jun. 7, 2001.

(51) Int. Cl.[7] .............................................. G01N 31/00
(52) U.S. Cl. .................. 422/100; 422/82.05; 422/68.1; 422/99; 436/174; 436/179; 436/180; 137/15.18
(58) Field of Search ............................ 422/68.1, 82.05, 422/99, 100; 436/174, 179, 180; 137/15.18

(56) References Cited

U.S. PATENT DOCUMENTS

| | | | |
|---|---|---|---|
| 3,449,938 A | 6/1969 | Giddings | 73/23 |
| 3,568,692 A | 3/1971 | Metzger et al. | 137/81.5 |
| 4,946,795 A | 8/1990 | Gibbons et al. | 436/179 |
| 5,077,017 A | 12/1991 | Gorin et al. | 422/100 |
| 5,230,866 A | 7/1993 | Shartle et al. | 422/103 |
| 5,376,252 A | 12/1994 | Ekström et al. | 204/299 R |
| 5,427,946 A | 6/1995 | Kricka et al. | 435/291 |
| 5,595,712 A | 1/1997 | Harbster et al. | 422/129 |
| 5,637,469 A | 6/1997 | Wilding et al. | 435/7.21 |
| 5,690,763 A | 11/1997 | Ashmead et al. | 156/60 |
| 5,698,299 A | 12/1997 | Schmidt et al. | 428/209 |
| 5,726,404 A | 3/1998 | Brody | 200/81 R |
| 5,757,482 A | 5/1998 | Fuchs et al. | 356/246 |
| 5,834,314 A | 11/1998 | Gates et al. | 436/52 |

(Continued)

FOREIGN PATENT DOCUMENTS

| | | |
|---|---|---|
| EP | 1 106 244 A2 | 6/2001 |
| WO | WO 97/00125 | 1/1997 |
| WO | WO 99/09042 | 2/1999 |

(Continued)

OTHER PUBLICATIONS

Ehrfeld, W., et al., *Potentials and Realization of Microreactors*, "DECHEMA Monographs," vol. 132, VCH Verlagsgesellschaft, 1996, pp. 1–28.

(Continued)

*Primary Examiner*—Jill Warden
*Assistant Examiner*—Sam P. Siefke
(74) *Attorney, Agent, or Firm*—Vincent K. Gustafson

(57) ABSTRACT

Modular microfluidic systems includes a plurality of microfluidic modules, each capable of performing fluidic operations including, but not limited to, filtering, splitting, regulating pressure, mixing, metering, reacting, diverting, heating, cooling, and condensing are provided. The microfluidic modules are polymeric, stencil-based structures adapted to be coupled in sequence for performing biological or chemical synthesis, including, but not limited to, chemical and biological syntheses of organic, polymer, inorganic, oligonucleotide, peptide, protein, bacteria, and enzymatic products.

14 Claims, 20 Drawing Sheets

U.S. PATENT DOCUMENTS

| | | | |
|---|---|---|---|
| 5,846,396 A | 12/1998 | Zanzucchi et al. | 204/601 |
| 5,872,010 A | 2/1999 | Karger et al. | 436/173 |
| 5,904,424 A | 5/1999 | Schwesinger et al. | 366/336 |
| 5,921,678 A | 7/1999 | Desai et al. | 366/336 |
| 6,004,515 A | 12/1999 | Parce et al. | 422/100 |
| 6,030,581 A | 2/2000 | Virtanen | 422/68.1 |
| 6,043,080 A | 3/2000 | Lipshutz et al. | 435/287.2 |
| 6,074,725 A | 6/2000 | Kennedy | 428/188 |
| 6,117,396 A | 9/2000 | Demers | 422/100 |
| 6,156,273 A | 12/2000 | Regnier et al. | 422/70 |
| 6,190,034 B1 | 2/2001 | Nielsen et al. | 366/336 |
| 6,221,654 B1 | 4/2001 | Quake et al. | 435/287.3 |
| 6,235,471 B1 | 5/2001 | Knapp et al. | 435/6 |
| 6,264,892 B1 | 7/2001 | Kaltenbach et al. | 422/68.1 |
| 6,264,900 B1 | 7/2001 | Schubert et al. | 422/224 |
| 6,274,089 B1 | 8/2001 | Chow et al. | 422/101 |
| 6,296,020 B1 | 10/2001 | McNeely et al. | 137/806 |
| 6,306,590 B1 | 10/2001 | Mehta et al. | 435/6 |
| 6,331,439 B1 | 12/2001 | Cherukuri et al. | 436/174 |
| 6,444,461 B1 | 9/2002 | Knapp et al. | 435/283.1 |
| 6,494,230 B2 | 12/2002 | Chow | 137/827 |
| 6,494,614 B1 | 12/2002 | Bennett et al. | 366/336 |
| 6,533,840 B2 | 3/2003 | Martin et al. | 95/45 |
| 6,537,501 B1 | 3/2003 | Holl et al. | 422/101 |
| 6,537,506 B1 | 3/2003 | Schwalbe et al. | 422/130 |
| 6,561,208 B1 * | 5/2003 | O'Connor et al. | 137/15.18 |
| 6,601,613 B2 | 8/2003 | McNeely et al. | 137/833 |
| 2002/0076350 A1 | 6/2002 | Weigl et al. | 422/58 |
| 2002/0094533 A1 | 7/2002 | Hess et al. | 435/6 |

FOREIGN PATENT DOCUMENTS

| | | |
|---|---|---|
| WO | WO 99/17093 | 4/1999 |
| WO | WO 99/19717 | 4/1999 |
| WO | WO 99/33559 | 7/1999 |
| WO | WO 00/21659 | 4/2000 |
| WO | WO 00/72970 A1 | 12/2000 |
| WO | WO 01/04909 A1 | 1/2001 |
| WO | WO 01/09598 A1 | 2/2001 |
| WO | WO 01/28670 A1 | 4/2001 |

OTHER PUBLICATIONS

Kikutani, Y., et al., "Fabrication of a Glass Microchip with a Three–Dimensional Channel Network and its Application to a Single–Chip Combinatorial Synthetic Reactor," *Micro Total Analysis Systems*, J.M. Ramsey and A. van den Berg (eds.), 2001, Kluwer Academic Publishers, the Netherlands, pp. 161–162.

Knight, James B., et al., *Hydrodynamic Focusing on a Silicon Chip: Mixing Nanoliters in Microseconds*, "The American Physical Society," vol. 80, No. 17, Apr. 27, 1998, pp. 3863–3866.

Larsen, Ulrik Darling, et al., *Fast Mixing by Parallel Multilayer Lamination*, "Analytical Methods & Instrumentation, Special Issue uTAS," 1996, pp. 228–230.

Mensinger, H., et al., "Microreactor with Integrated Static Mixer and Analysis System," *Micro Total Analysis Systems*, A. van den Berg and P. Bergveld (eds.), 1995, Kluwer Academic Publishers, the Netherlands, pp. 237–243.

Branebjerg, Jens, et al., "Fast mixing by lamination," Proc. Micro Electro Mechanical Systems Workshop, pp. 441–446, IEEE (1996).

Deshmukh, Ajay A., et al. "Continuous Micromixer with Pulsatile Micropumps," Solid–State Sensor and Actuator Workshop, Hilton Head Island, SC, USA, Jun. 4–8, 2000, 73–6.

Martin, P.M., et al., *Laser micromachined and laminated microchannel components for chemical sensors and heat transfer applications*, "SPIE," vol. 3224, Sep. 26, 1997, pp. 258–265.

Manz, Andreas, et al., *Electroosmotic pumping and electrophoretic separations for miniaturized chemical analysis systems*, "J. Micromech. Microeng.," 1994, pp. 257–265.

Seller, Kurt, et al., *Electroosmotic Pumping and Valveless Control of Fluid Flow within a Manifold of Capillaries on a Glass Chip*, "Analytical Chemistry," vol. 66, No. 20, Oct. 15, 1994, pp. 3485–3491.

Tracey, M.C., et al., "Microfluidic Mixer Employing Temporally–Interleaved Liquid Slugs and Parabolic Flow," *Micro Total Analysis Systems*, J.M. Ramsey and A. van den Berg (eds.), 2001, Kluwer Academic Publishers, the Netherlands, pp. 141–142.

Liu, Robin H., et al., "Plastic In–Line Chaotic Micromixer for Biological Applications," *Micro Total Analysis Systems*, J.M. Ramsey and A. van den Berg (eds.), 2001, Kluwer Academic Publishers, the Netherlands, pp. 163–164.

Ehrfeld, et al., *Injection of Many Small Substreams of One Component into a Main Stream of Another Component*, "Microreactors," Wiley–VCH Verlagsgesellschaft MBH, $1^{st}$ edition, 2000, pp. 53–55.

Johnson, Timothy J., et al., *Rapid Microfluidic Mixing*, "Analytical Chemistry," vol. 74, No. 1, Jan. 1, 2002, pp. 45–51.

Verpoorte, Elisabeth M.J., et al., "Silicon–Based Chemical Microsensors and Microsystems," *Interfacial Design and Chemical Sensing*, 1994, American Chemical Society, Chapter 21, pp. 244–254.

* cited by examiner

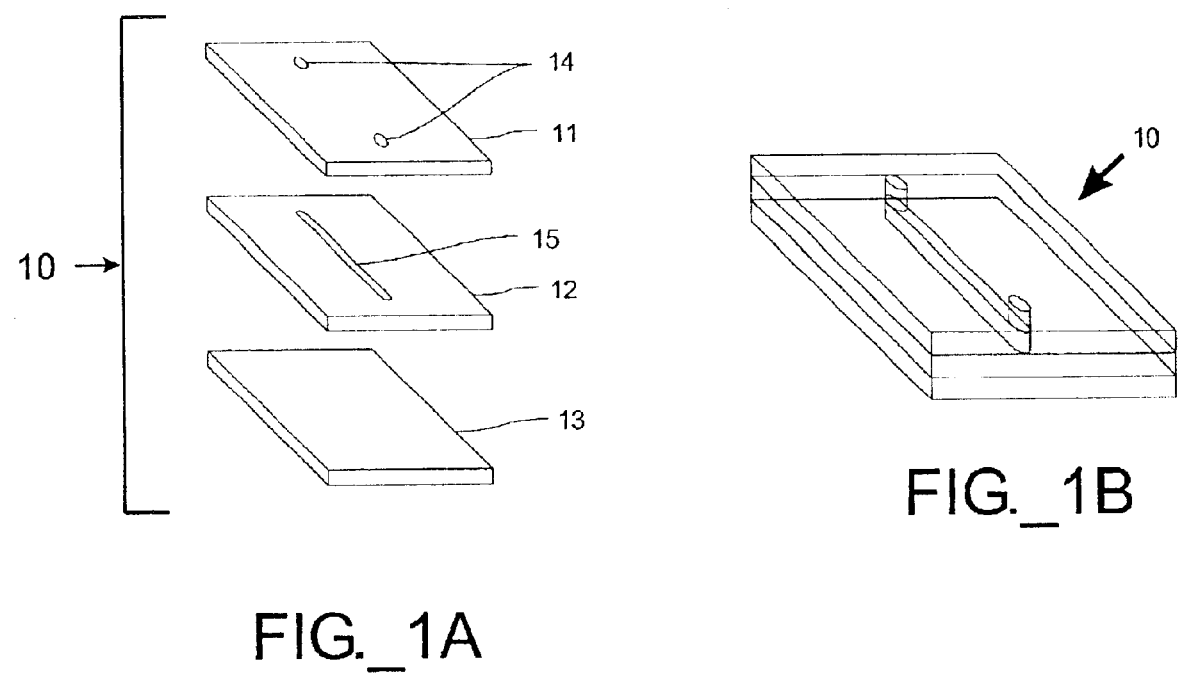
FIG._1A
FIG._1B

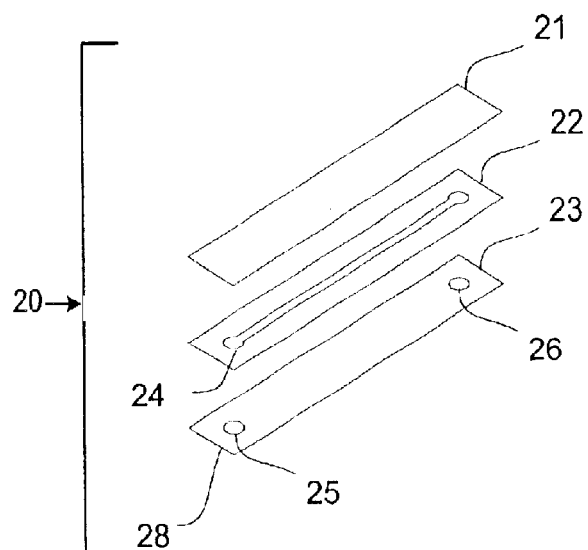
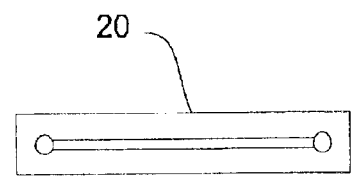
FIG._2A
FIG._2B
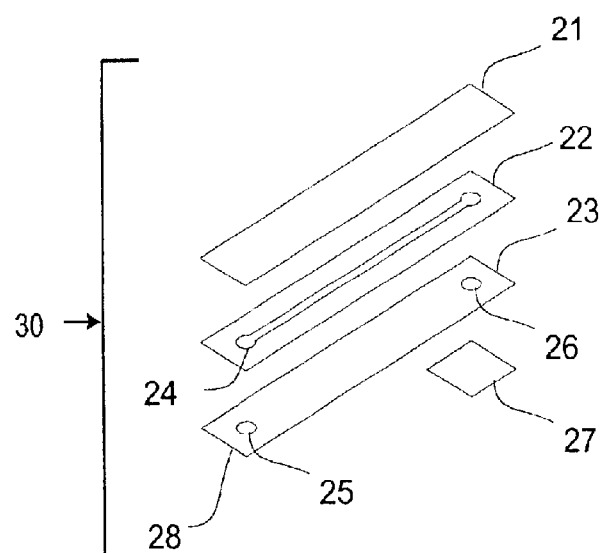
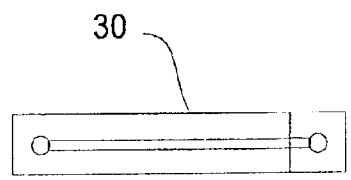
FIG._2C
FIG._2D

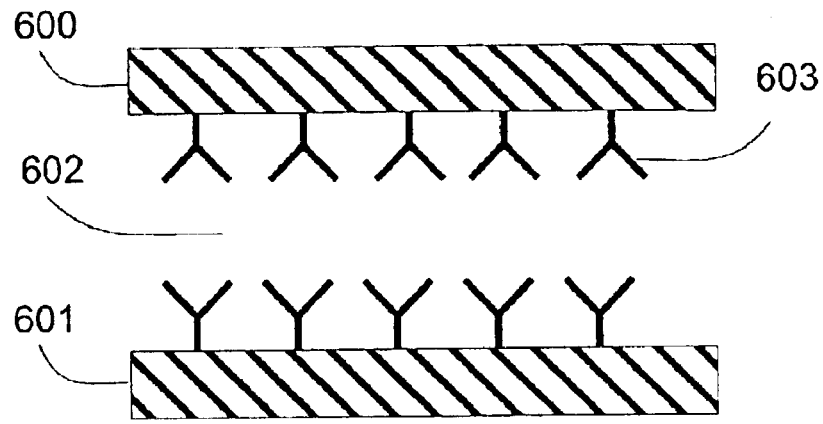
FIG._3A
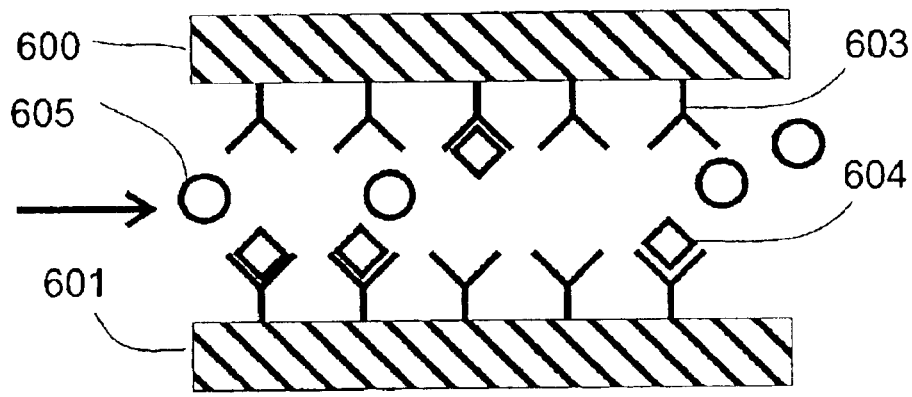
FIG._3B
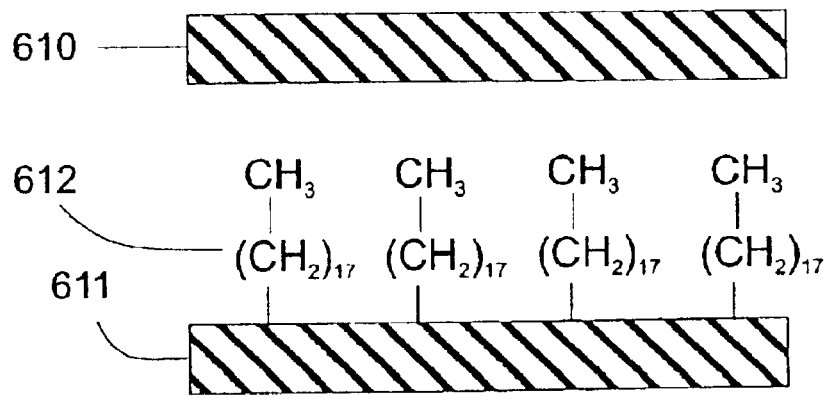
FIG_3C

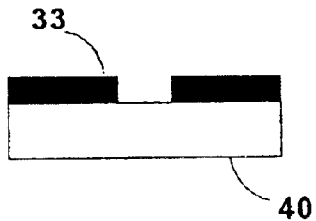
FIG._4A
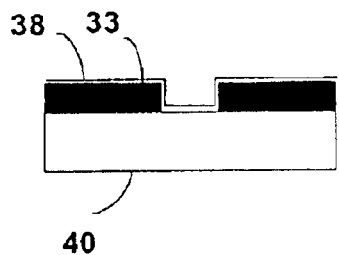
FIG._4B
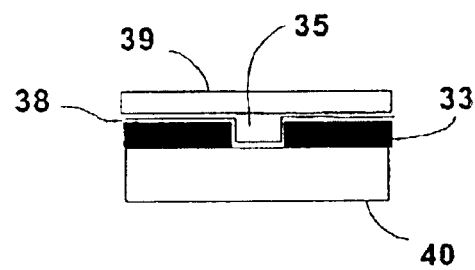
FIG._4C
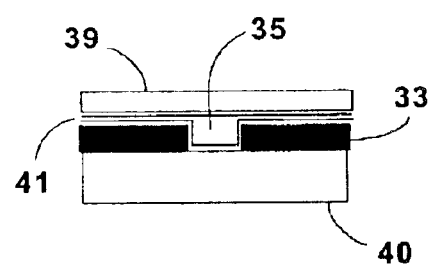
FIG._4D
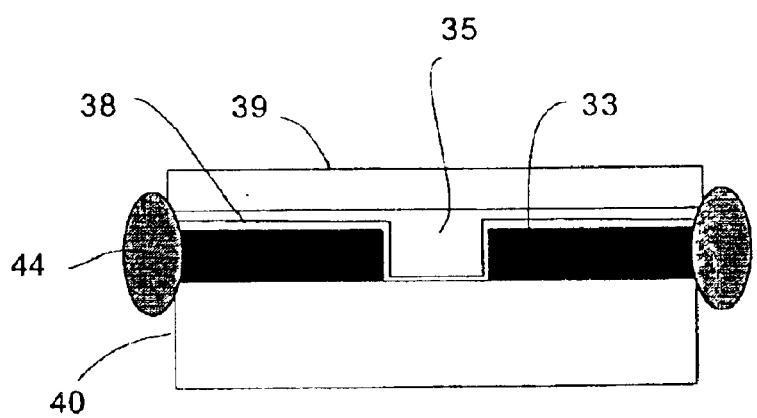
FIG._4E

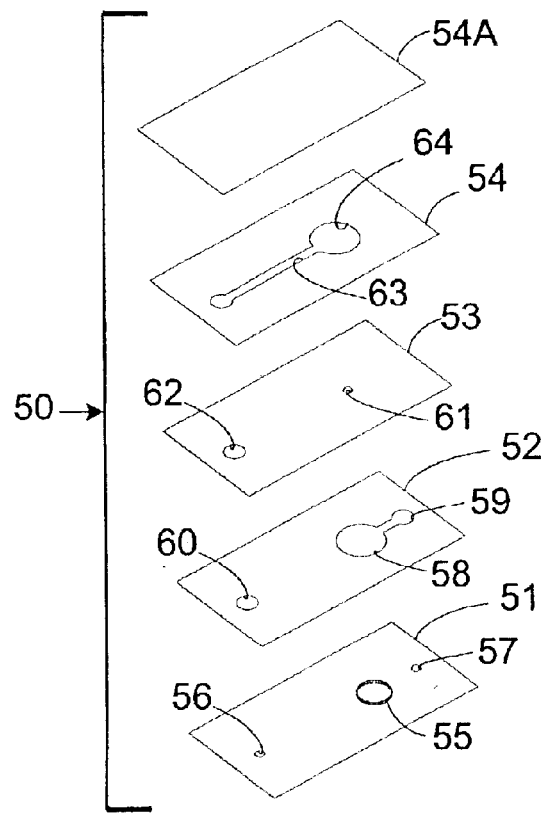
FIG._5A
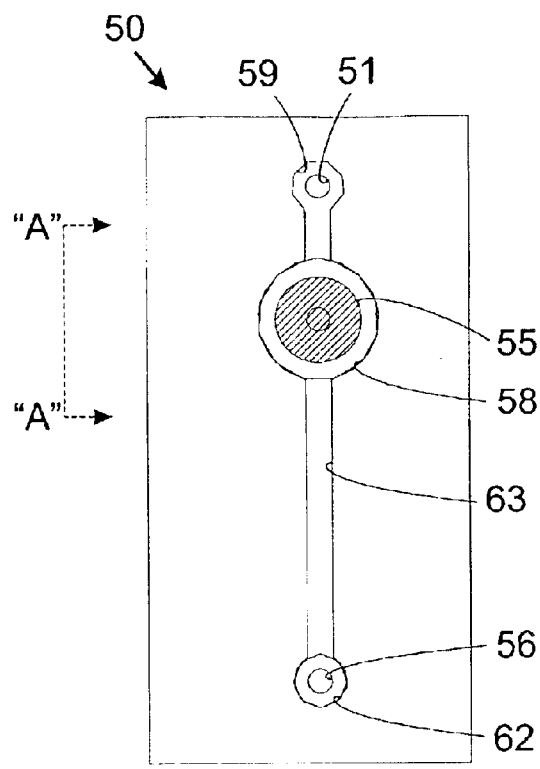
FIG._5B
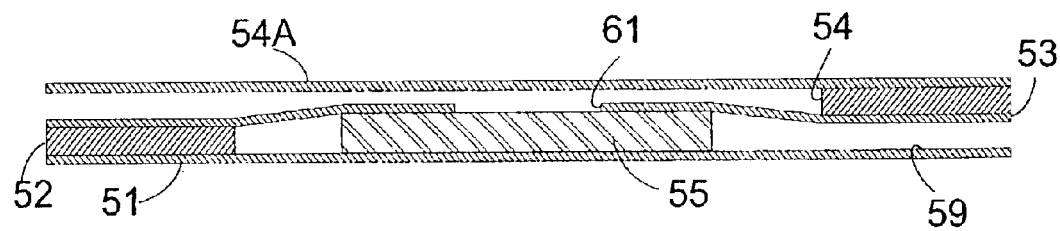
FIG._5C

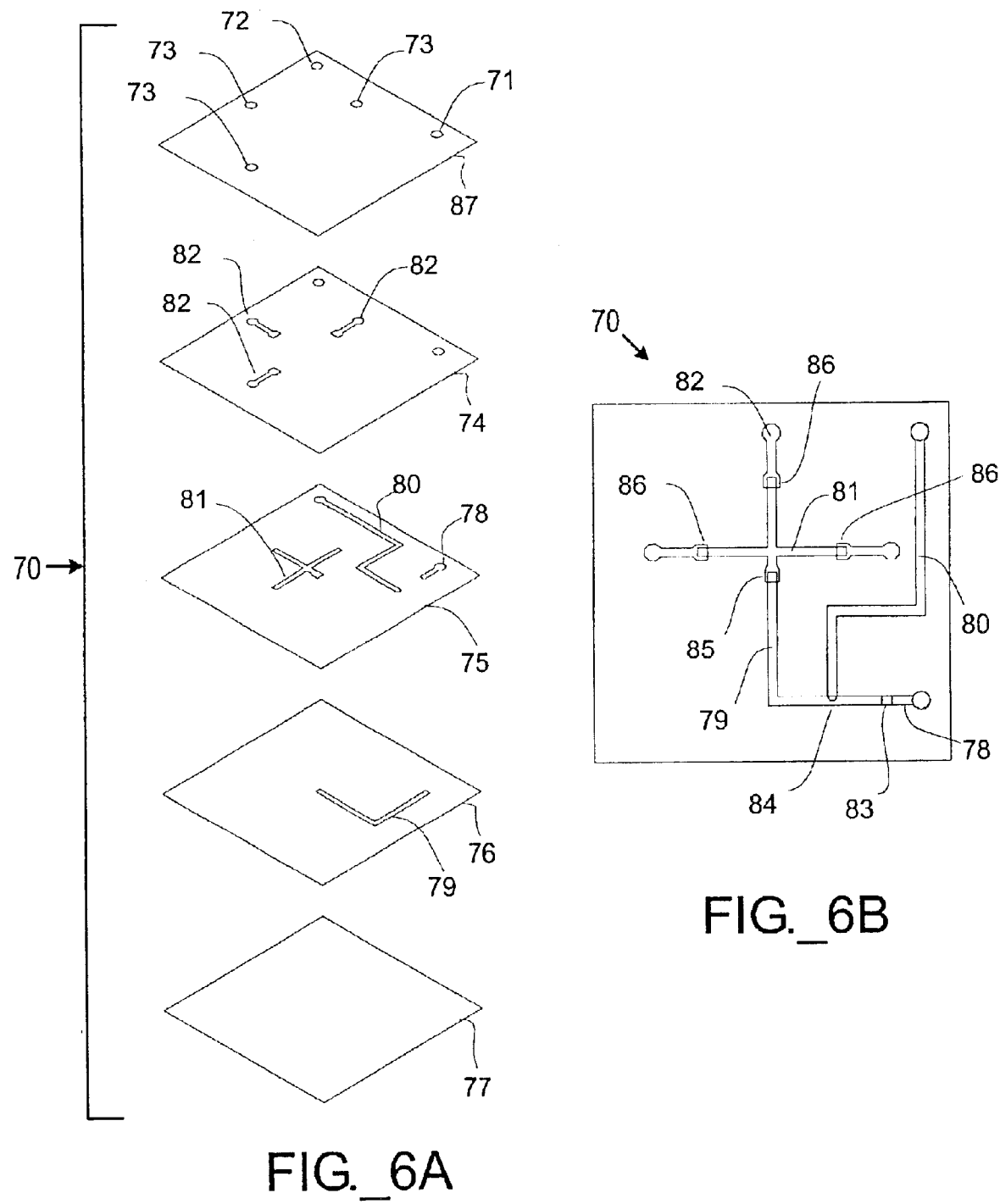
FIG._6A
FIG._6B

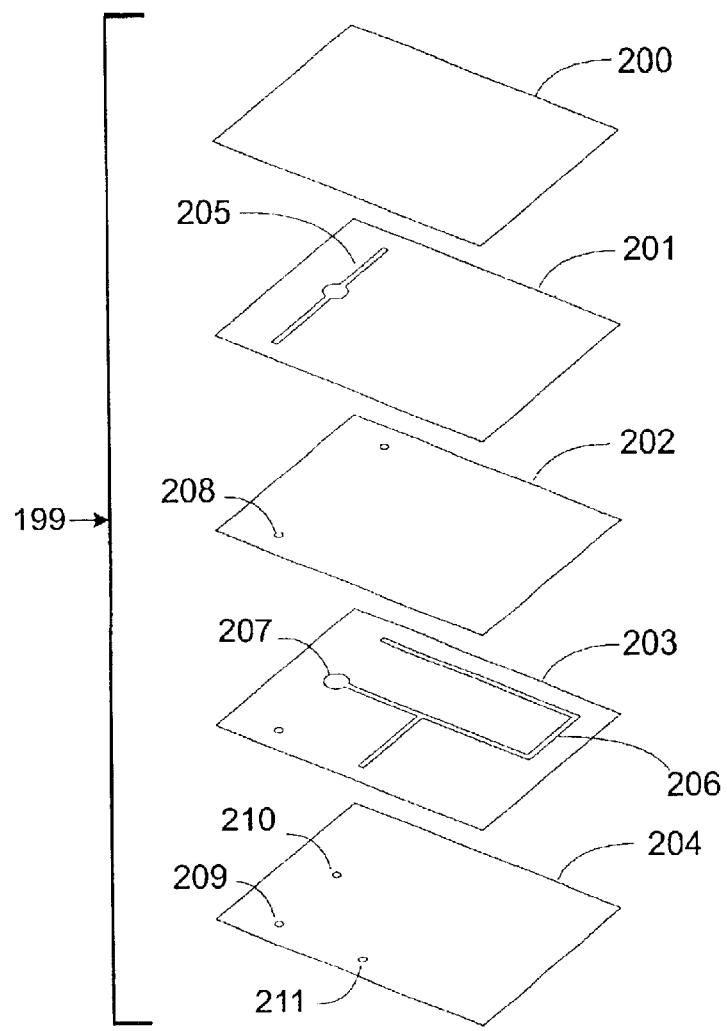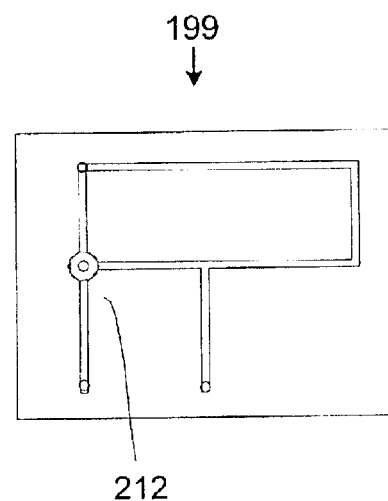
FIG._7A
FIG._7B

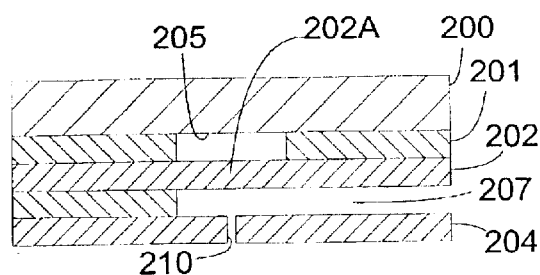
FIG._7C
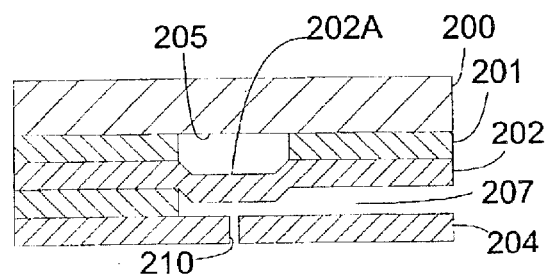
FIG._7D
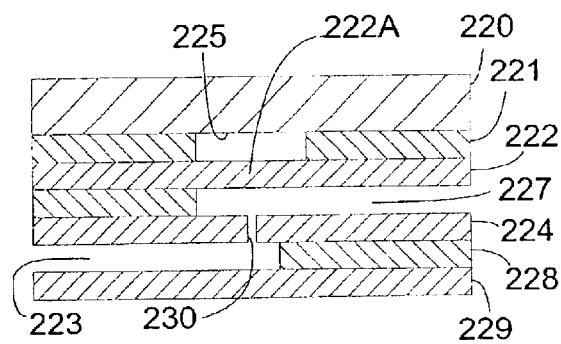
FIG._7E
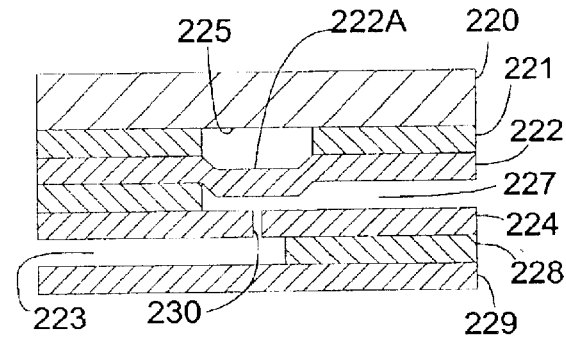
FIG._7F

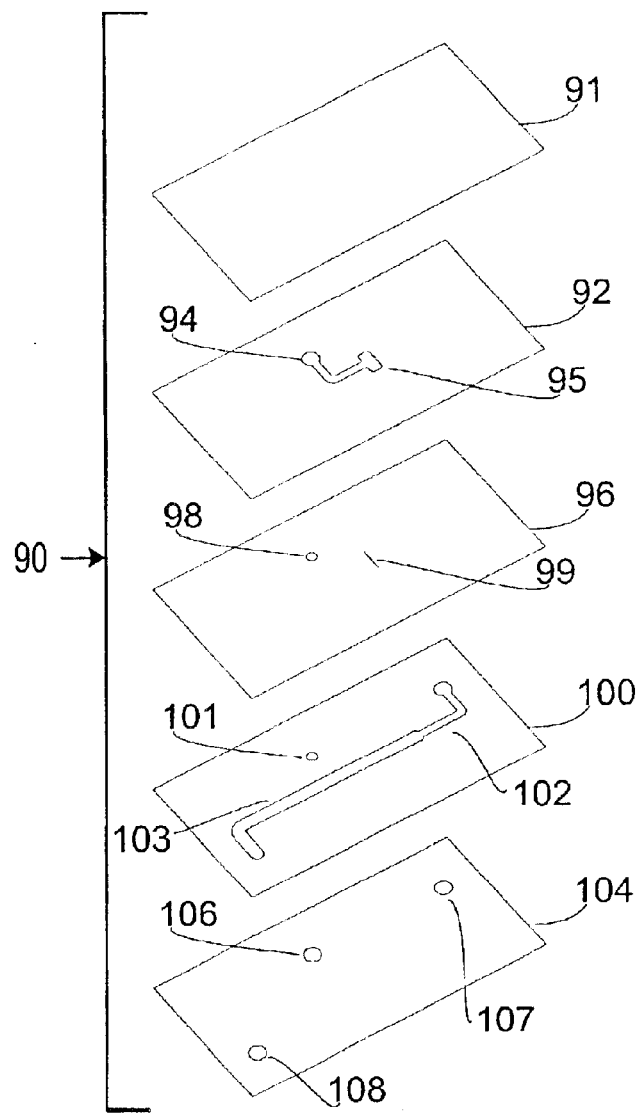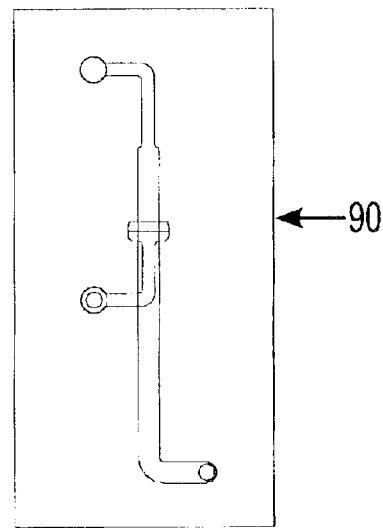
FIG._8A
FIG._8B

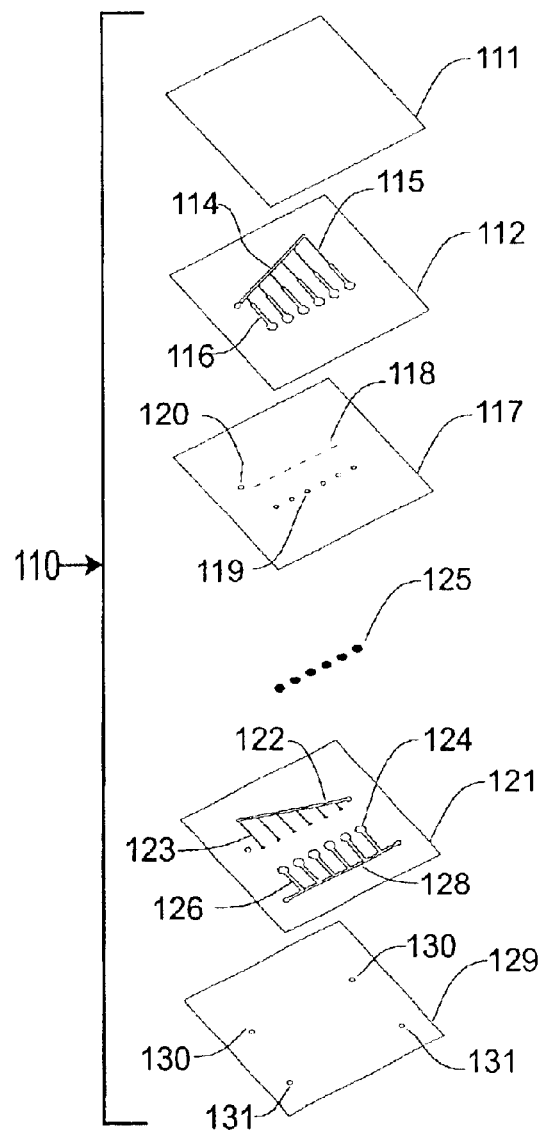
FIG._9A
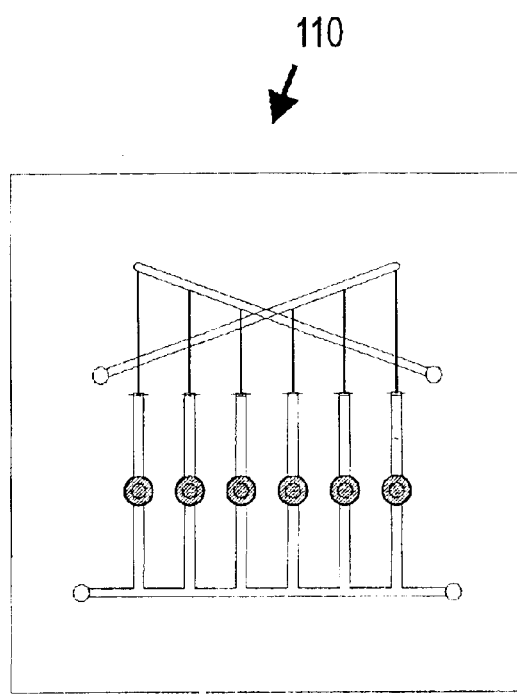
FIG._9B

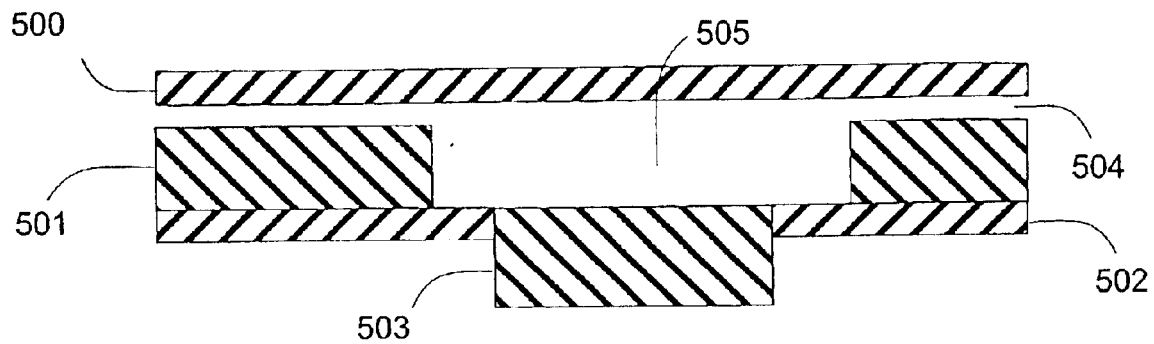
FIG._10A
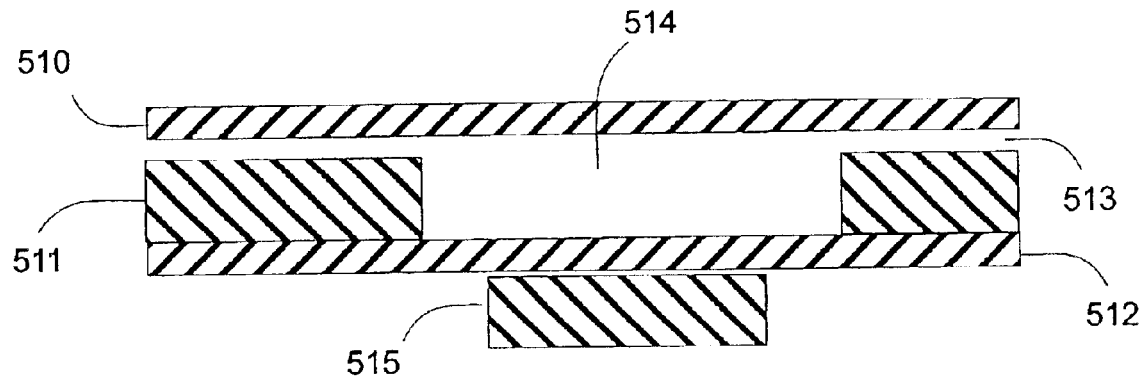
FIG._10B
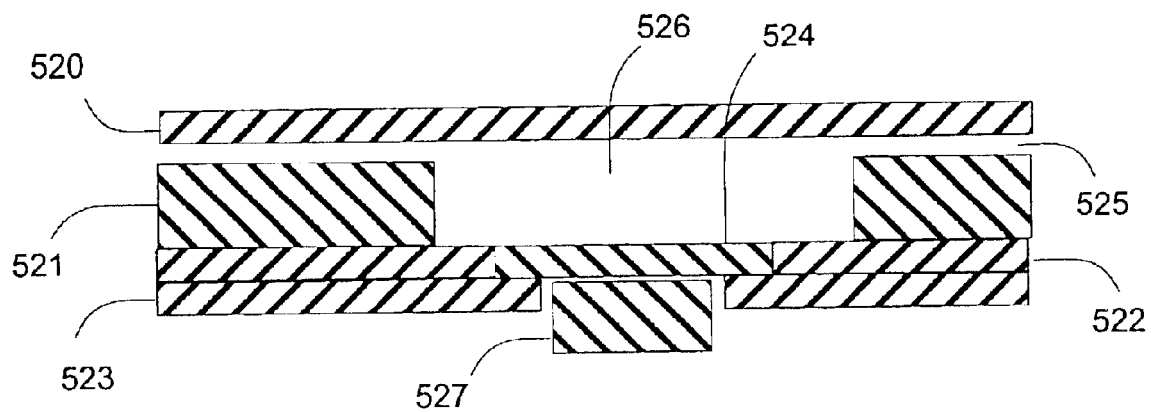
FIG._10C

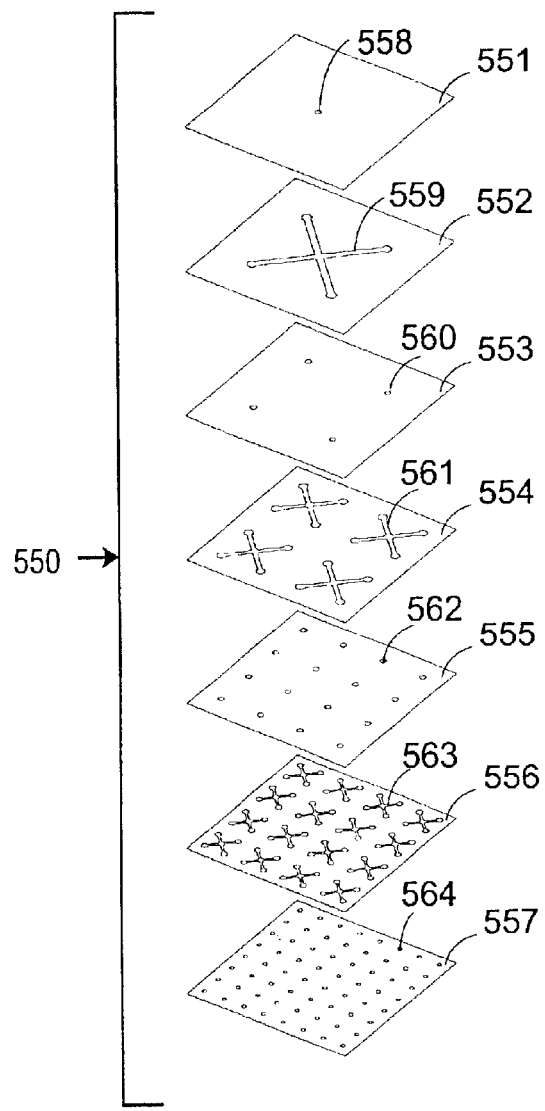
FIG._11A
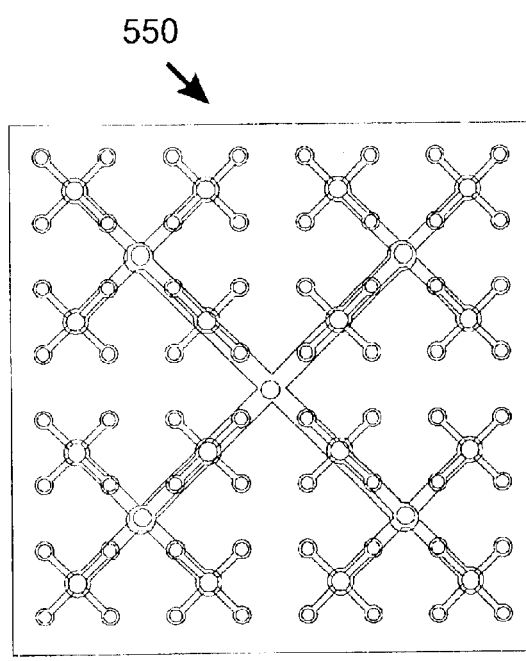
FIG._11B

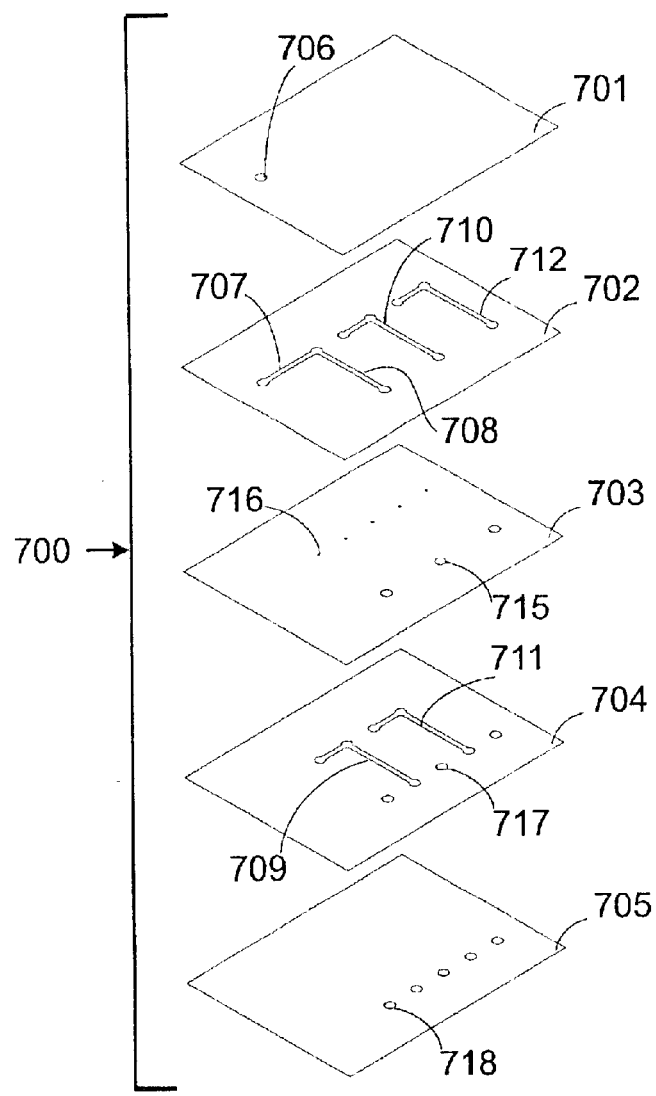
FIG._12A
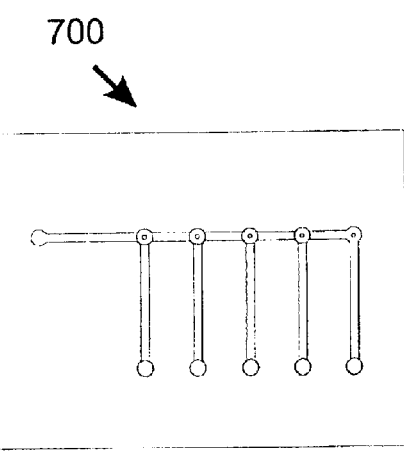
FIG._12B

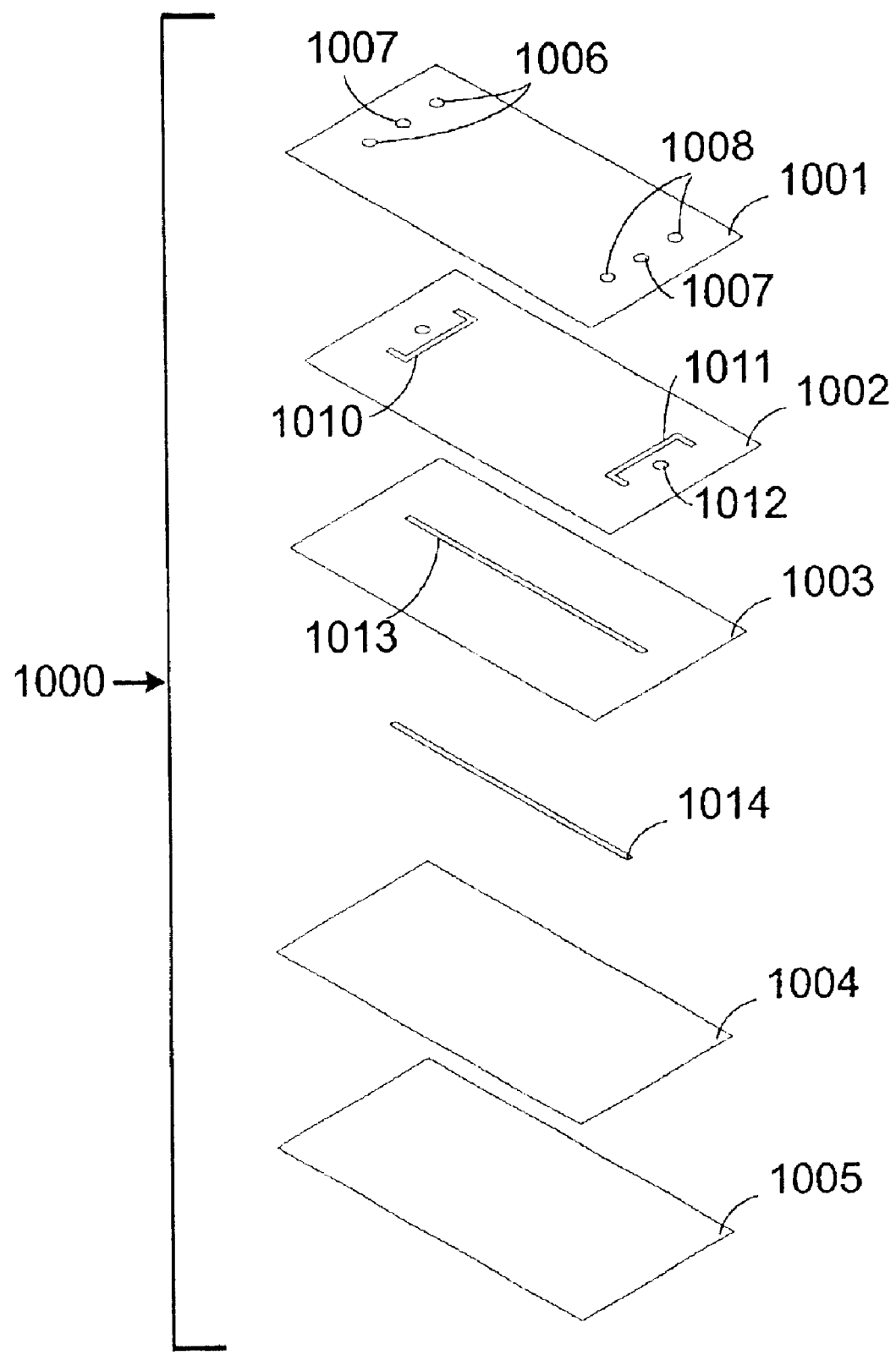
FIG._13

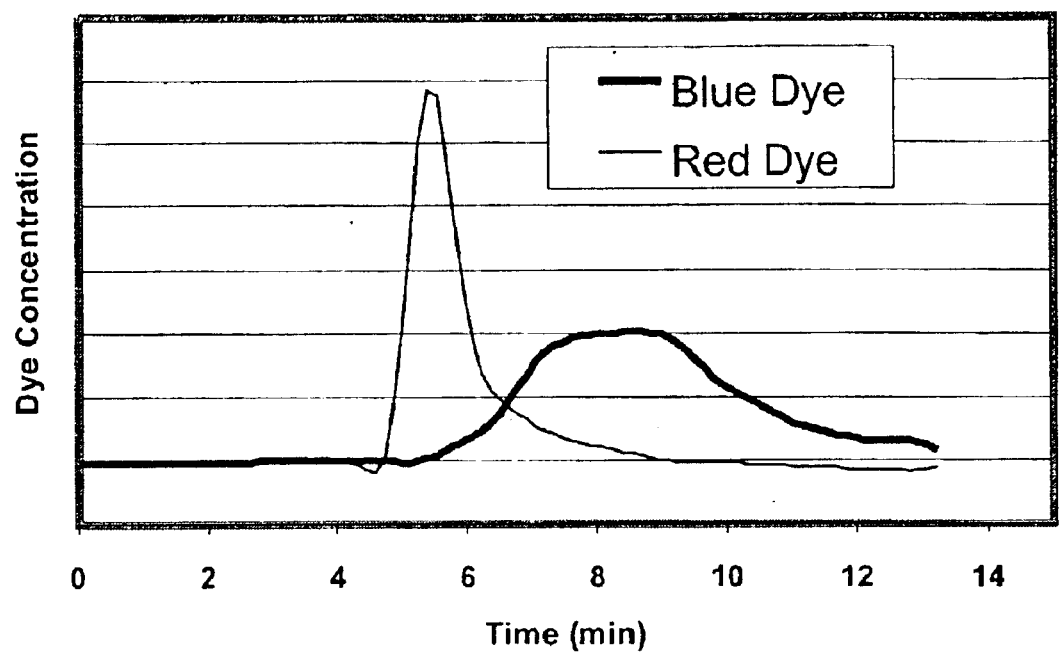
FIG._14A
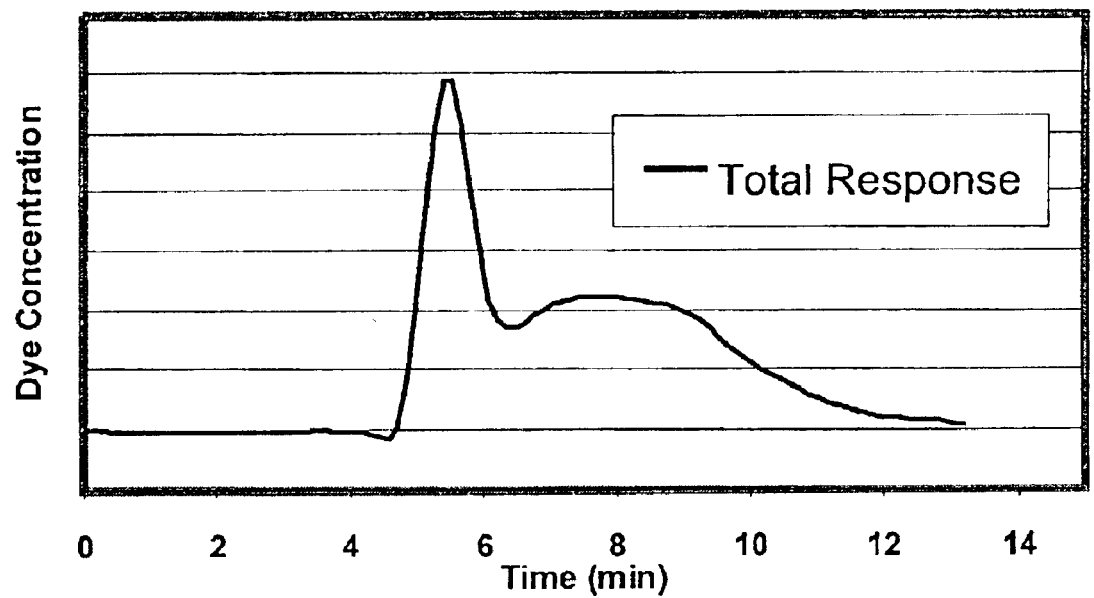
FIG._14B

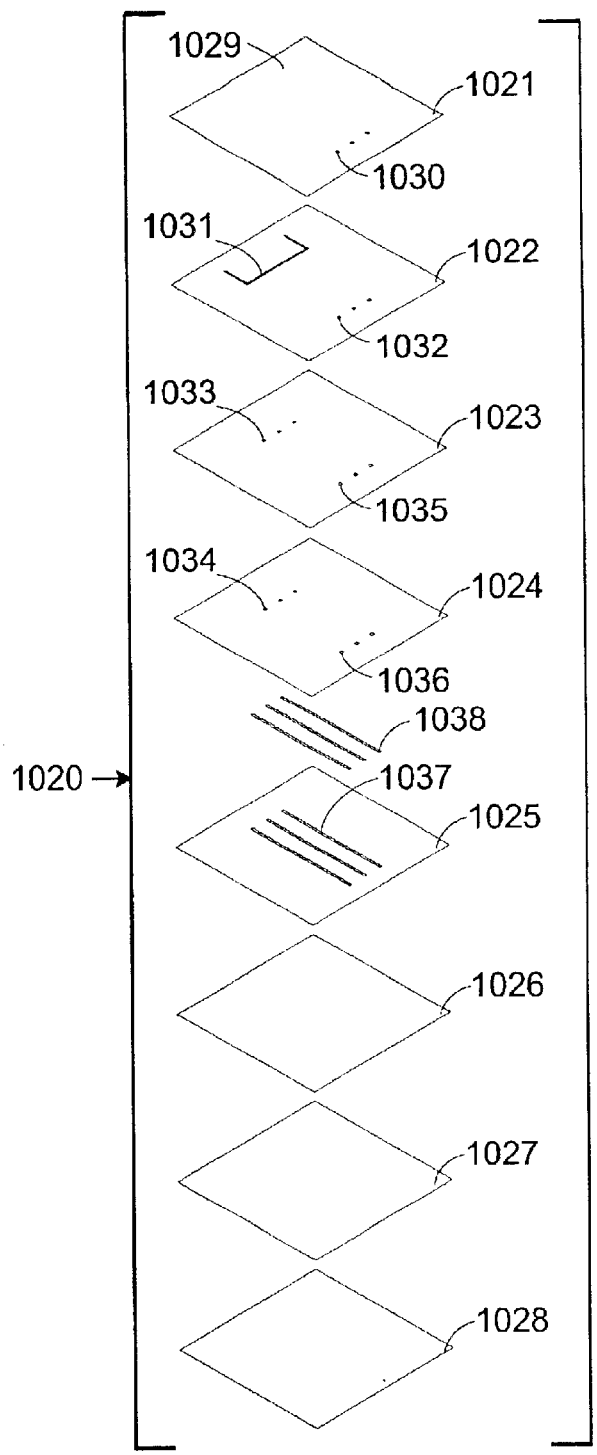
FIG._15A
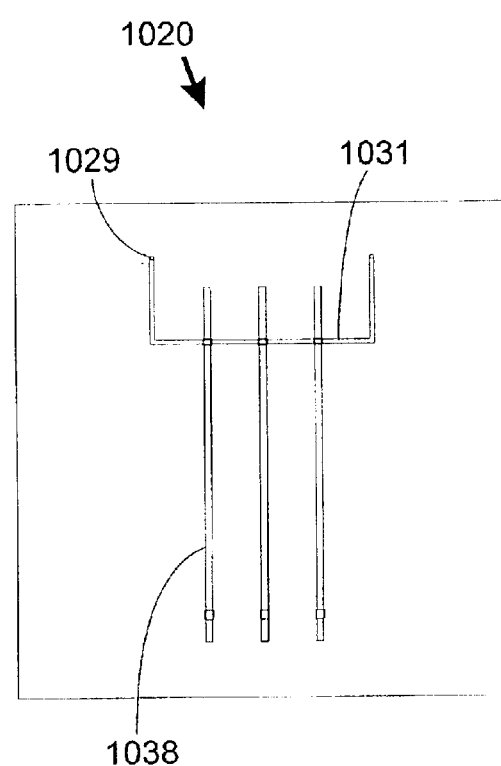
FIG._15B

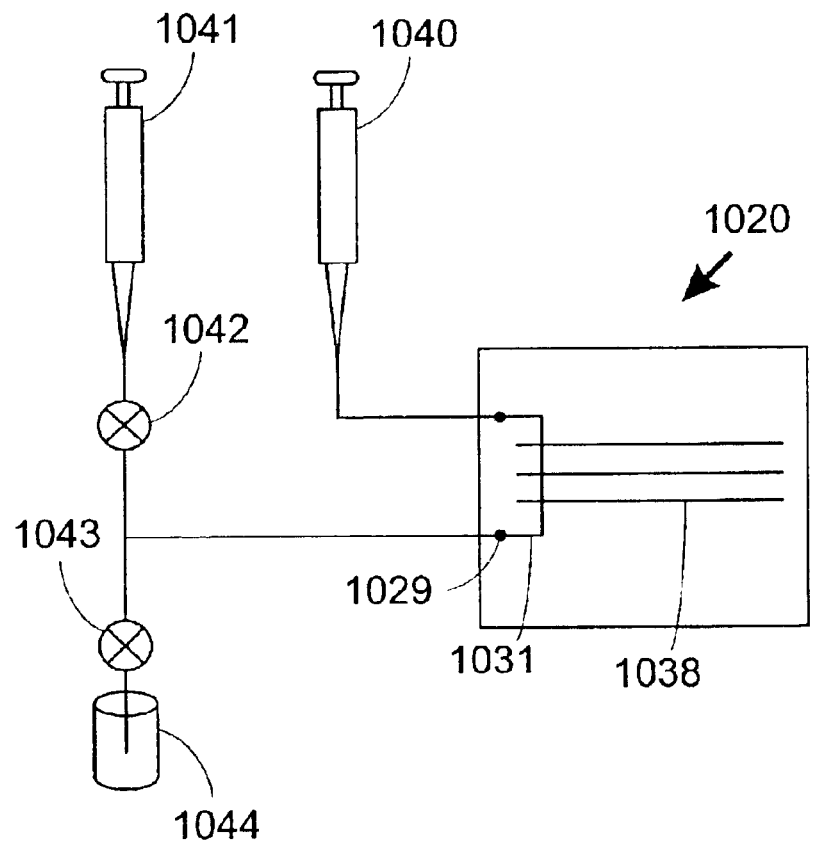
FIG._16
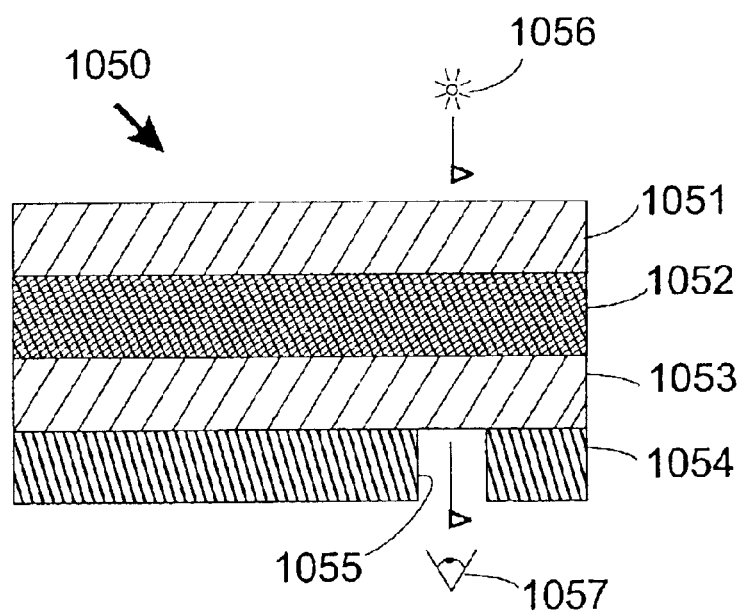
FIG._17

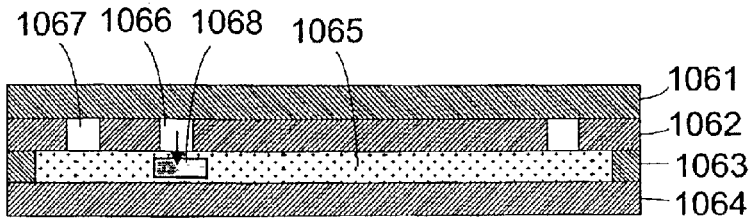
FIG._18A
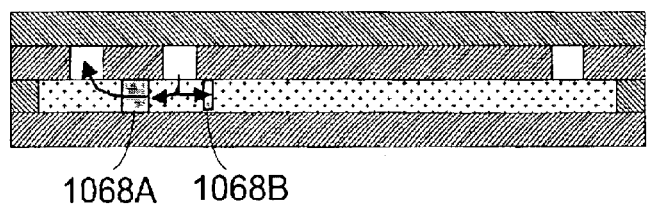
FIG._18B
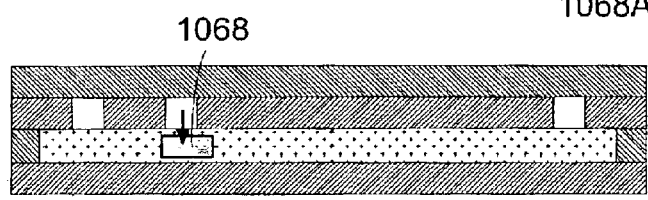
FIG._18C
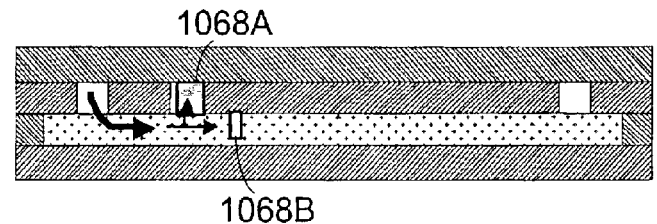
FIG._18D
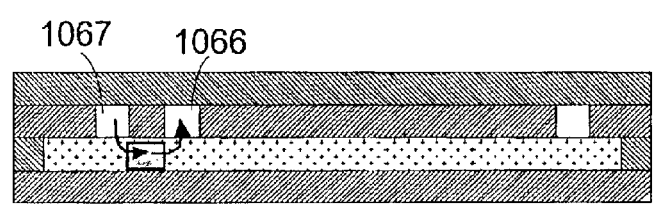
FIG._18E
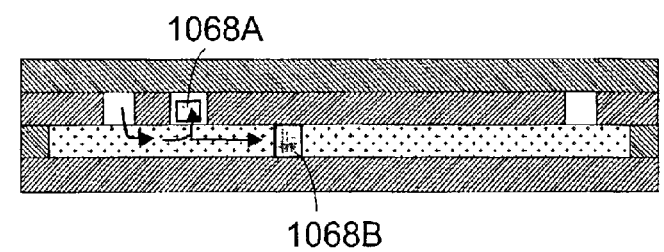
FIG._18F

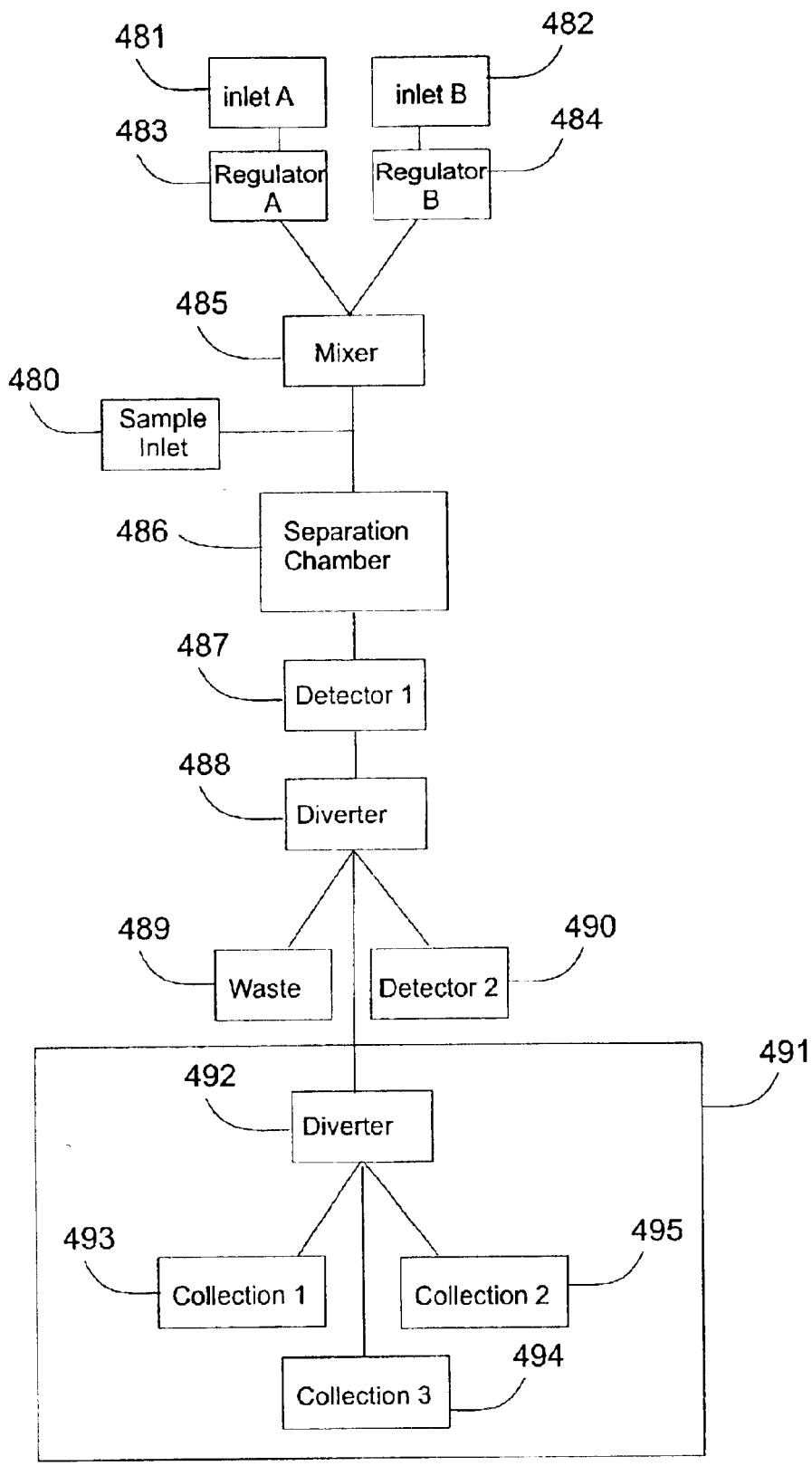
FIG._19

MICROFLUIDIC ANALYTICAL DEVICES AND METHODS

STATEMENT OF RELATED APPLICATION(S)

This application claims priority to U.S. Provisional Patent Application Ser. No. 60/296,897, filed Jun. 7, 2001 and currently pending.

FIELD OF THE INVENTION

The present invention relates to microfluidic analysis devices and methods for their use and manufacture. These devices and methods are useful in performing microfluidic-scale chemical and biological analyses including separations and detections.

BACKGROUND OF THE INVENTION

There has been a growing interest in the manufacture and use of microfluidic systems for the acquisition of chemical and biological information. In particular, when conducted in microfluidic volumes, complicated biochemical reactions may be carried out using very small volumes of liquid. Among other benefits, microfluidic systems increase the response time of reactions, minimize sample volume, and lower reagent consumption. When volatile or hazardous materials are used or generated, performing reactions in microfluidic volumes also enhances safety and reduces disposal quantities.

Traditionally, microfluidic devices have been constructed in a planar fashion using techniques that are borrowed from the silicon fabrication industry. Representative systems are described, for example, in some early work by Manz et al. (Trends in Anal. Chem. (1990) 10(5): 144–149; Advances in Chromatography (1993) 33: 1–66). In these publications, microfluidic devices are constructed by using photolithography to define channels on silicon or glass substrates and etching techniques to remove material from the substrate to form the channels. A cover plate is bonded to the top of the device to provide closure. Miniature pumps and valves can also be constructed to be integral (e.g., within) such devices. Alternatively, separate or off-line pumping mechanisms are contemplated.

More recently, a number of methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy et al., Analytical Chemistry (1998) 70: 4974–4984; McCormick et.al., Analytical Chemistry (1997) 69: 2626–2630), or by building a traditional injection molding cavity for plastic devices. Some molding facilities have developed techniques to construct extremely small molds. Components constructed using a LIGA technique have been developed at the Karolsruhe Nuclear Research center in Germany (see, e.g., Schomburg et al., Journal of Micromechanical Microengineering (1994) 4: 186–191), and commercialized by Micro-Parts (Dortmund, Germany). Jenoptik (Jena, Germany) also uses LIGA and a hot-embossing technique. Imprinting methods in PMMA have also been demonstrated (see, Martynova et.al., Analytical Chemistry (1997) 69: 4783–4789) However, these techniques do not lend themselves to rapid prototyping and manufacturing flexibility. Additionally, the foregoing references teach only the preparation of planar microfluidic structures. Moreover, the tool-up costs for both of these techniques are quite high and can be cost-prohibitive.

Various conventional tools and combinations of tools are used for separations and detections when performing analyses in conventional macroscopic volumes. Such tools include, for example: filters, metering devices, columns, valves, sample injectors, heaters, coolers, mixers, splitters, diverters, and electrodes (such as are used to induce electrokinetic flow and to perform electrophoretic separations). Attempts to conduct separations or detections in microfluidic volumes have been stifled by difficulties such as making such tools in microfluidic scale and then integrating such tools into microfluidic devices. Another difficulty is accurately measuring stoichiometric microfluidic volumes of reagents and solvents to perform analyses on a microfluidic scale. Additionally, difficulties in rapidly prototyping microfluidic devices are compounded by attempts to incorporate multiple analytical tools.

When working with fluids in conventional macroscopic volumes, achieving effective mixing between two or more fluid streams is a relatively straightforward task. Various conventional strategies may be employed to induce turbulent regions that cause fluid streams to mix rapidly. For example, active stirring or mixing elements (e.g., mechanically or magnetically driven) may be employed. Alternatively, special geometries may be employed in flow channels to promote mixing without the use of moving elements. One common example of the use of special geometries includes the addition of baffles to deflect flowing fluid streams and thereby promote turbulence.

Applying conventional mixing strategies to microfluidic volumes is generally ineffective, impractical, or both. To begin with, microfluidic systems are characterized by extremely high surface-to-volume ratios and correspondingly low Reynolds numbers (less than 2000) for most achievable fluid flow rates. At such low Reynolds numbers, fluid flow within most microfluidic systems is squarely within the laminar regime, and mixing between fluid streams is motivated primarily by the phenomenon of diffusion— typically a relatively slow process. In the laminar regime, using conventional geometric modifications such as baffles is generally ineffective for promoting mixing. Moreover, the task of integrating moveable stirring elements and/or their drive means in microfluidic devices would be prohibitively difficult using conventional means due to volumetric and/or cost constraints, in addition to concerns regarding their complexity and reliability. In light of these limitations, it would be desirable to provide a microfluidic mixer that could rapidly mix fluid streams without moving parts, in a minimal space, and at a very low construction cost. An ideal fluid mixer would further be characterized by minimal dead volume to facilitate mixing of extremely small fluid volumes.

SUMMARY OF THE INVENTION

In one aspect of the invention, a microfluidic device for passively mixing at least two fluids for analysis comprises a plurality of device layers. The plurality of device layers define a first fluidic input, a first junction or manifold region in fluid communication with the first fluidic input, a first plurality of unequal impedance branch channels in fluid communication with the first junction or manifold region, a second fluidic input, a second junction or manifold region in fluid communication with the second fluidic input, a second plurality of unequal impedance branch channels in fluid communication with the second junction or manifold region and a plurality of mixer regions in fluid communication with the first plurality of unequal impedance branch channels and the second plurality of unequal impedance branch channels.

The plurality of mixer regions, the first plurality of unequal impedance branch channels, and the second plurality of unequal impedance branch channels are disposed within the plurality of device layers so as to permit simultaneous and combination of a first fluid and a second fluid in a plurality of different predetermined mixing ratios. The plurality of device layers further define a detection region in fluid communication with the plurality of mixer regions.

This and other aspects and advantages of the invention will be apparent to the skilled artisan upon review of the following description, drawings and claims.

BRIEF DESCRIPTION OF THE DRAWINGS

FIG. 1A is an exploded perspective view of a microfluidic device fabricated with stencil layers. FIG. 1B is a top view of the assembled device of FIG. 1A.

FIG. 2A is an exploded perspective view of a microfluidic coupler fabricated with stencil layers. FIG. 2B is a top view of the assembled device of FIG. 2A. FIG. 2C is an exploded perspective view of a microfluidic coupler fabricated with stencil layers including a semi-permeable membrane. FIG. 2D is a top view of the assembled device of FIG. 2C.

FIG. 3A is a cross-sectional view (not to scale) of a microfluidic channel coated with chemical moieties. FIG. 3B is a cross-sectional view of the microfluidic channel of FIG. 3A in operation. FIG. 3C is a cross-sectional view (not to scale) of a microfluidic channel that has been coated with a common chromatography material: —(CH2)17-CH3.

FIGS. 4A–4E side, cross-sectional views of the fabrication of a stencil layer microfluidic device with a coating or sealing layer on a channel therein.

FIG. 5A is an exploded perspective view of microfluidic device with a filter. FIG. 5B is a top view of the device of FIG. 5A. FIG. 5C is a side cross-sectional view of a portion of the device of FIGS. 5A–5B taken along line "A"—"A".

FIG. 6A is an exploded perspective view of a microfluidic device according to the invention for dividing and metering a fluid sample. FIG. 6B is a top view of the assembled device of FIG. 6A.

FIG. 7A is an exploded perspective view of a five-layer microfluidic device capable of delivering a relatively constant flow rate of fluid over a large range of pressures. FIG. 7B is a top view of the assembled device of FIG. 7A. FIG. 7C is a cross-sectional view of a portion of the microfluidic device of FIGS. 7A–7B with the regulatory region in the open position. FIG. 7D provides the same cross-sectional view as FIG. 7C, but with the regulatory region in the closed position. FIG. 7E is a cross-sectional view of an alternate embodiment of the device of FIGS. 7A–7B that includes a separate control channel for regulating fluid flow with the regulatory region in the open position. FIG. 7F provides the same cross-sectional view as FIG. 7E, but with the regulatory region in the closed position.

FIG. 8A is an exploded perspective view of microfluidic mixing device. FIG. 8B is a top view of the device of FIG. 8A.

FIG. 9A is an exploded perspective view of microfluidic mixing device. FIG. 9B is a top view of the device of FIG. 9A.

FIGS. 10A–10C are partial cross-sectional views of various embodiments of heating and/or cooling elements in use with microfluidic devices.

FIG. 11A is an exploded perspective view of a multi-layer microfluidic splitting device. FIG. 11B is a top view of the assembled device of FIG. 11A.

FIG. 12A is an exploded perspective view of a microfluidic fraction collector. FIG. 12B is a top view of the assembled device of FIG. 12A.

FIG. 13 is an exploded perspective view of a five-layer microfluidic device for performing liquid chromatography.

FIGS. 14A–14B are graphs showing the data produced during operation of the device of FIG. 13.

FIG. 15A is an exploded perspective view of a multi-column microfluidic liquid chromatography device. FIG. 15B is a top view of the assembled device of FIG. 15A.

FIG. 16 is a schematic diagram of a liquid chromatography system incorporating the device of FIGS. 15A–15B.

FIG. 17 is a cross-sectional schematic diagram of detection system for the liquid chromatography device of FIGS. 15A–15B.

FIGS. 18A–18F are schematic cross-sectional views of a multi-layer microfluidic separation device showing various operational methods to split an injection plug between a separation column and a waste outlet.

FIG. 19 is a schematic diagram of a microfluidic analytical device that provides both separation and detection capabilities.

DETAILED DESCRIPTION

Figure 20:
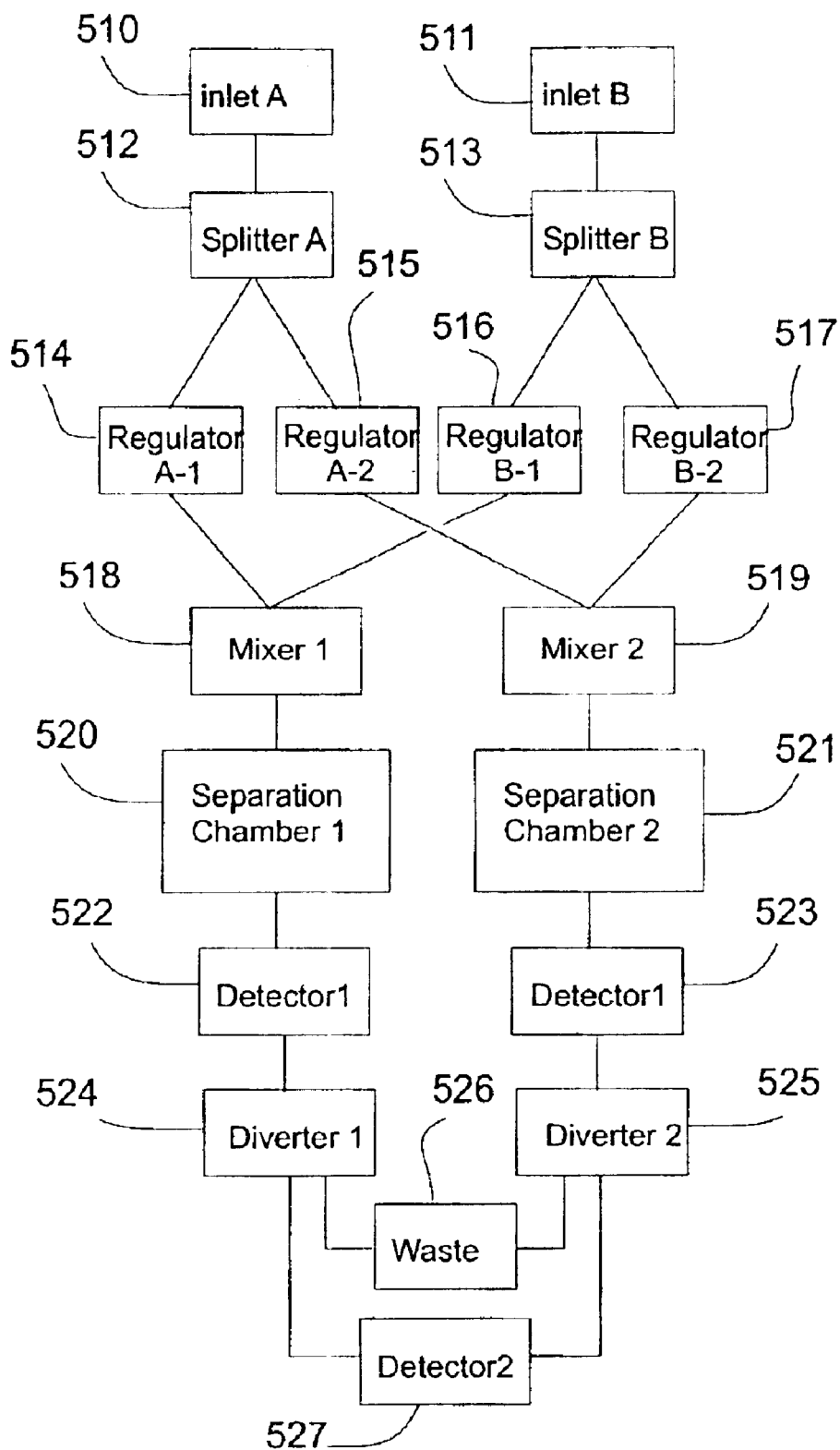
FIG. 20 is a schematic diagram of a parallel processing microfluidic analytical device that provides both separation and detection capabilities.

Definitions:

The term "channel" or "chamber" as used herein is to be interpreted in a broad sense. Thus, it is not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" and "chambers" may be filled or may contain internal structures comprising, for example, valves, filters, and similar or equivalent components and materials.

The term "detection" as used herein is to be interpreted broadly to include qualitative and/or quantitative methods. Analytical techniques may be used to detect analytes either within a microfluidic device according to the present invention or outside the device. Classes of detection methods that may be used include, for example, optical, electrochemical, spectroscopic, and spectrometric methods.

The term "microfluidic" as used herein is to be understood, without any restriction thereto, to refer to structures or devices through which fluid(s) are capable of being passed or directed, wherein one or more of the dimensions is less than 500 microns. Additionally, such devices can be constructed using any of the materials described herein, as well as combinations of such materials and similar or equivalent materials.

The term "microfluidic system" as used herein refers to a microfluidic path, often including one or more microfluidic devices, capable of carrying or holding fluids. A microfluidic system may be composed of one or more subsystems.

The term "parallel processing" as used herein refers to multiple microfluidic systems on a given contiguous device wherein some or all of the systems are in fluid communication with one another.

The term "self-adhesive tape" as used herein refers to a material layer or film having an integral adhesive coating on one or both sides.

The term "separation" as used herein is to be interpreted broadly, so as to include separation, extraction, and purification.

The term "stencil" as used herein refers to a preferably substantially planar material layer or sheet through which one or more variously shaped and oriented portions have been cut or removed through the entire thickness of the layer, and which removed portions permit substantial fluid movement within the layer (as opposed to simple throughholes or vias for transmitting fluid from one layer to another layer). The outlines of cut or removed portions form the lateral boundaries of microstructures that are formed when a stencil is sandwiched between other layers such as substrates or other stencils.

Preferred Embodiments

Certain embodiments of the present invention utilize microfluidic devices comprising sandwiched stencils. Referring to FIGS. 1A–1B, a simple microfluidic device 10 is constructed by sandwiching a stencil 12 between two substrates 11, 13. Referring to FIG. 1A, an enclosed channel 15 is constructed by defining a channel 15 in the stencil layer 12 and sandwiching the stencil 12 between two substrates 11, 13, here represented by a bottom substrate 13 and a top substrate 11. Alternatively, stencil layers may be stacked directly on one another, rather than being immediately sandwiched between substrates. Substrates and stencil layers may be either rigid or flexible. Inlet and outlet apertures may be provided in the device 10. In this embodiment, two apertures 14 are defined in the top substrate 11. The assembled device is shown in FIG. 1B. Inlet and outlet apertures can be open to the environment surrounding the device, can lead to an adjacent stencil and/or substrate layer, or can lead to another modular device by way of a coupling device (discussed in further detail hereinafter).

Microstructures (e.g., channels and chambers) can be formed in one or more stencils either before or after being placed on a substrate. Stencil and substrate layers with various microstructures may be stacked or layered to provide a complex microfluidic device. One or more materials are preferably used to coat, seal, and/or adhere the stencil and/or substrate layers, to assist in forming useful microstructures. In certain embodiments, a stencil is shaped prior to placement on a substrate, by cutting or removing a portion of the stencil material of the appropriate size, shape, and orientation to form microstructures. A stencil can be cut, for example, using a die-cutter, which is preferably automated. Alternatively, cutting of stencils may be performed using a laser cutter. In a preferred embodiment, a stencil is automatically cut using a die cutter or laser cutter that is controlled by a computer. In another preferred embodiment, cuts are made using a rotary cutter or printer press, or any high throughput auto-aligning equipment. These devices are sometimes referred to as converters.

In one embodiment utilizing sandwiched stencil microfluidic devices, a stencil layer comprises single-sided or double-sided adhesive tape. Substrates may also be formed from tape. A portion of the tape (of the desired shape and dimensions) can be cut and removed to form, for example, a channel, a chamber, or an entry/exit port. The tape stencil can then be placed on or between one or more substrates or other stencil layers. In one embodiment, stencil layers are stacked on each other. In this embodiment, the thickness or height of the channels can be varied by simply varying the thickness of the stencil (e.g., the tape carrier and adhesive thereon).

Various types of tape are useful in the above embodiment. The type of adhesive can be varied to accommodate the application, as can the thickness and composition of any underlying (or overlying) carrier. Suitable tapes for use in the present invention can have various methods of curing or activation, including pressure-sensitive tapes, temperature-activated tapes, chemically-activated tapes, and optically-activated tapes, among others. Various adhesives are useful, including, for example, rubber-based adhesives, acrylic-based adhesives, and gum-based adhesives. The materials used to carry the adhesives are also numerous. Examples of suitable tape carrier materials include Mylar®, polyester, and nylon, although others (including those mentioned hereinafter) may be used. The thickness of the carrier may be varied.

The chemical nature of the individual stencil and substrate materials, and thus the chemistry of a microstructure used within a microfluidic module can be "tuned" for particular applications. A stencil material can be hydrophilic, hydrophobic, or ionic in nature. Stencil layers and substrate layers can be flexible. In various preferred embodiments, a stencil and substrate materials are selected from the group consisting of vinyl, filter material, paper or fabric, foil, and foam or foam sheets. In other preferred embodiments, stencil and substrate layers are formed from polymeric materials. Suitable polymers include, but are not limited to, polycarbonate, acrylic, polyurethane, polyethylene, including high-density polyethylene (HDPE) and ultra-high molecular weight polyethylene (UHMW), polypropylene (PP), polyvinylidene fluoride (PVDF), polytetrafluoroethylene (PTFE), nylon, polyethersulfone (PES), acetal copolymers, polyesterimides, polysulfones, polyphenylsulfones, ABS, polyvinylidene fluoride, polyphenylene oxide, and derivatives thereof. Further suitable materials include MYLAR™, polyester, polyimide (e.g., KAPTON™). Composite materials may also be used. In an especially preferred embodiment, the polymer is a fluorinated polymer, since fluorinated polymers often have superior resistance to aggressive solvents such as organic solvents. Additional materials will be mentioned hereinafter. Selection of particular materials for a desired application depends on numerous factors including: the types, concentrations, and residence times of substances (e.g., analytes, sample matrix, and solvents) present in regions of a device; temperature; pressure; pH; optical properties; and chromatographic effect. When necessary to withstand high pressures, microfluidic devices fabricated according to various methods provided herein may further be externally clamped by conventional means.

Referring to FIGS. 2A–2D, a microfluidic coupling device useful with certain embodiments of the present invention may be fabricated from multiple material layers. A microfluidic coupling device generally provides a fluidic interface to one or more external (preferably microfluidic) devices. Referring to FIGS. 2A–2B, a microfluidic coupling device 20 is formed from a first substrate layer 21 having an upper surface defining the top of the device 20, and from a second substrate layer 23 having a lower surface defining the bottom of the device 20. The coupling device also has at least one stencil layer 22 disposed between the first and second substrate layers 21, 23. The stencil layer 21 has at least one channel 24 formed in it, with at least one dimension less than about 500 microns. Preferably, each layer forming a microfluidic coupling device such as the device 20 has a height of between about 1 and 500 microns and a length and width each at least 100 times larger than the height. Various materials may be used for the stencil and substrate layers. In one example, stencil layer 21 is constructed from a MYLAR® material, stencil layer 22 from double sided tape and stencil layer 23 from single sided tape with a MYLAR® backing. In this manner, the top and bottom surfaces of the channel 24 are both MYLAR® material. The channel 24 is in fluid communication with a first aperture 25 defined in the second substrate layer 23. Although not required in all cases, the device 20 contains a second aperture 26 in the second substrate layer 23. The second aperture 26 is in fluid communication with the channel 24. In some embodiments, the second aperture may be located in the first substrate layer 21. Alternatively, all or a part of either substrate layer can be a semi-permeable membrane that allows gas to pass, but substantially prevents liquid from crossing. Other membranes that trap solid particles such as precipitate but permit liquid to pass may be used. In addition to coupling microfluidic modules or devices, microfluidic couplers may be used to collect samples.

Preferably, an adhesive is used to connect a microfluidic coupler with one or more external devices. More preferably, an adhesive used to couple the microfluidic coupler to the microfluidic device is non-permanent, so as to permit a coupler to be attached to a microfluidic device, fluid to be transferred by way of the coupler, and then the coupler to be removed. Using removable adhesive with a coupler facilitates removal of a sample from a device by removing a sample-containing coupler from a device. In another preferred embodiment, coupling between a microfluidic coupler and a microfluidic device is established with a tacky substance such as silicone.

In one embodiment utilizing a microfluidic coupler, the microfluidic coupling device is flexible. An entire microfluidic coupling device can be constructed of various films, papers, tapes, plastics and the like such that the coupling device is flexible. Flexibility can aid in alignment of the microfluidic coupling device to another microfluidic device or can facilitate coupling between two external microfluidic devices. The material used also can be malleable. Malleability aids in sealing a microfluidic coupler with another device, especially in cases where one or more mating surfaces are uneven.

The microfluidic coupler 20 of FIG. 2A can be constructed such that the lower surface of the second substrate 23 is adhesive so as to mate with another device (not shown) along one or more of the apertures 25, 26. The device 20 may also be constructed such that the upper surface of the first substrate layer 21 is adhesive. In one embodiment, a coupler has two apertures, one in the first substrate layer and one in the second substrate layer, and both the upper surface and lower surface are adhesive. Such an embodiment allows for rapid connection of the coupler to other microfluidic devices. The adhesive used may be either permanent or removable. In such an embodiment, the coupler may further include a backing layer removably adhered to the adhesive lower surface of the second substrate or a portion of that surface. The backing material protects the adhesive material until such a time as the microfluidic coupling device is to be attached to another microfluidic device. The backing material can be any suitable plastic, paper or foil.

A microfluidic coupler may also include a semipermeable membrane 27 covering the second aperture 26, as shown in FIGS. 2C–2D. The semipermeable membrane 27 allows gases to pass, but will not substantially allow a liquid to pass. For example, a suitable semipermeable membrane will allow air to pass through it, but will not allow water to pass. A suitable semipermeable membrane can have pores of a sufficient size to achieve the desired effect. In one embodiment, the semipermeable membrane is a polymeric material with a pore size of less than about 75 microns, and preferably less than about 10 microns. Examples of such filter materials include X-7744, a 7 $\mu$m pore size T3 sheet from Porex Technologies (Fairburn, Ga.) and GORETEX®-type materials.

In one embodiment, the first aperture 25 of the microfluidic device 20 shown in FIG. 2A is used as an inlet port, and the second aperture 26 is used as a vent for air escape. Alternatively, the second aperture 26 can be used as an exit port rather than a vent. The inlet port 25 can be directly coupled to another microfluidic device (not shown) using an adhesive. An adhesive can either be on the coupling device 20 or on the microfluidic device to which the coupling device 20 is to be attached.

In another preferred embodiment, porous materials can be used at an outlet of a microfluidic coupler to add impedance to the system. These materials can be chosen so that their properties are such that they have slight resistances to air or gas, and very large resistances to fluid flow. For example, pore size and material composition can be selected to produce the desired effects and impedances. Different materials can be used at various outlets. In this manner, the outlet materials can be used in conjunction with the overlap impedances to produce preferential fluid flow within a device.

In one embodiment, the bottom surface 28 of the microfluidic coupler 20 may be covered with an adhesive material along the inlet port 25 that allows the inlet port 25 to be connected to an outlet port of an external microfluidic device (not shown). Alternatively, the coupler surface 28 may be non-adhesive and the surface of the external microfluidic device to be coupled may be adhesive. In an alternative embodiment, mating surfaces of both the coupler and the external microfluidic are adhesive.

Adhesive can be placed on the bottom surface 28 of the microfluidic coupling device 20 in a number of ways. In a preferred embodiment, the bottom surface 28 of stencil layer 23 is inherently adhesive, such as an adhesive tape. In other embodiments, a coating is placed on the bottom surface 28 either before or after assembly. This coating can be accomplished in a number of ways, including spin coating, spray coating, etc.

When aggressive solvents such as organic solvents will be used with a microfluidic module or device according to the present invention, it is desirable to construct the module or device using relatively inert materials. Preferable construction materials include, but are not limited to fluorinated polymers (including, for example, FEP and PTFE), polypropylene, and polyethylene. In preferred embodiments constructed from multiple material layers, including those produced with sandwiched stencil methods, however, inert materials are challenging to work with because they are difficult to bind together. Specifically, these materials are usually characterized by low surface energies. To raise the surface energies of such materials to promote bindability, they may be surface treated. Desirable methods of surface treatment include: corona/plasma discharge; chemical treatment; and physical treatment. In a preferred embodiment, a microfluidic device was constructed employing a direct bonding method by heating sandwiched 2-mil layers of corona-treated FEP using a hot press at approximately 430° F. and 60 psi for approximately 40 seconds. In a more preferred embodiment, plasma-treated fluorinated polymers may be used.

In embodiments utilizing adhesives to bond layers of a microfluidic device intended for use with aggressive solvents, relatively inert adhesives are preferably used. Such adhesives include epoxies, acrylics (including UV-curable acrylics), polyurethanes, hot-melt adhesives, and certain rubber-based adhesives. Additionally, the adhesive bond line exposed to solvent in the resulting device is preferably thin to minimize interaction between the solvent and the adhesive.

In a preferred embodiment, a stencil layer is a flexible or elastomeric material, such as silicone, viton, or rubber, so as to enable tools including valving and pumping mechanisms. Pressure or mechanical force can be applied to a flexible layer to cause local bending or deformation, thereby blocking or partially obstructing a channel or chamber located above or below the flexible layer.

In a preferred embodiment, material forming a stencil is applied onto the substrate in only certain desired areas using printing techniques, such as, for example, silk screening. The material is then "cured" to form the channels and/or chambers. Examples include the use of an activatable or curable polymer as the stencil material. Another example is the use of paint or ink as the material. One example is the use of a Thick Medium heat-set acrylic from Genesis Artist Colors (Indianapolis, Ind.). In another embodiment, the entire surface of one of the substrates is coated with the stencil material. The stencil is then cured in areas where it is to remain and the rest of the material can be removed. In this embodiment, a curable epoxy material may be used. In a more preferred embodiment, the epoxy is a UV-curable epoxy. Alternatively, a two-part epoxy can be used, where the first part is patterned into place and the entire device is then soaked in the second part that only adheres to the stencil material in certain areas.

In a preferred embodiment, a sealant coat can serve to both coat and seal a microstructure. Referring to FIGS. 4A–4D, at least part of the surface of a stencil and/or substrate can be coated with a layer of sealant coat material. A cover plate substrate (which is preferably substantially planar during manufacture) can be layered upon the stencil to "cap" or complete the microstructure defined between the substrates. In FIG. 4C, the cover plate substrate is not coated. In FIG. 4D, the cover plate substrate is coated with a sealant coat material, which can be the same as or different than the other coatings used within the device. Referring to FIG. 4E, dabs of epoxy may be added to help adhere cover plate substrate, substrate, and stencil together. The epoxy can be added either before or after the sealant coat material has been cured. In another preferred embodiment, the layers of the device may be mechanically compressed (such as using clamps), separately or in addition to other device sealing methods. For example, gaskets can be used in conjunction with a compression device to help seal the microstructures. Mechanical sealing methods are especially desirable where coating materials do not serve to seal a microstructure.

Numerous suitable sealant coat materials having various desired properties can be used. The sealant coat material can be chemical and/or biological in nature, and can be hydrophobic or hydrophilic, depending on the application. Solids, liquids, gels and powders, or combinations thereof, can be used. Materials capable of carrying a surface charge can be used, as can neutral species. Sealants or coatings may serve additional functions, such as to provide filtration or impedance regions within a channel. Specific examples of coating materials suitable for use in the present invention include Teflon®, Liquin®, Avatrel®, silicone, silicone mixtures, epoxies (including rubber masks), glue, liquid polymers, polymeric dispersions, plastics, liquid acrylic, paint, metals, oils, waxes, foams, photoresist, varnish, solder, and glass. Sealants can be chosen to protect a device from degradation by specific solvents or reactive molecules. Fluorinated polymers have excellent resistance to various solvents and chemicals, including organic solvents, and may be used. Examples include Teflon®, Avatrel®, polyvinylidene fluoride (PVDF), THV Fluorothermoplastic (Dyneon, St. Paul Minn.), Hostaflon TF 5035 (Dyneon), fluorinated ethylene propylene (FEP), polytetrafluoroethlyene (PTFE), and perfluoroalkoxy (PFA), among others. Alternatively, other coating materials can be used that specifically resist certain classes of solvents. Classes of solvents that may be used with devices according to the present invention include but are not limited to alcohols, aromatics, halogenated solvents (for example chlorinated solvents such as dichloromethane), ethers, polar protic, polar aprotic, hydrocarbon, and aqueous. Aqueous solvents may be acidic, basic, or neutral.

In a preferred embodiment, the sealant coat material is a polymer, such as, for example, polyethlyene glycol and cyanoacrylate. In other preferred embodiments, the coating material is biological in nature. Advantageously, in various applications, the biological coating material can be used to either promote or prevent adherence of materials. In certain embodiments, a biological coating material (e.g., a ligand) that specifically binds to certain biological materials is advantageously employed. Examples of biological coating materials useful with the present invention include proteins, antibodies, lipids, cells, tissues, nucleic acids, and peptides. More specific examples include avidin, streptavidin, polylysine, and enzymes. Other materials include lysis buffer for lysing cells and solid reagents. In another example, channels are heparinized to prevent clotting of blood samples. In certain embodiments, the coating materials are used to selectively bind materials that are present in the samples. In another preferred embodiment, these catalytic materials are enzymatic in nature. Further In another embodiment, solid buffer materials are introduced to buffer a sample once it is injected.

The sealant coat material(s) can be deposited using one or more of a number of techniques. In a preferred embodiment, the sealant coat material(s) are spin-deposited onto a given substrate and/or stencil using a spinner or rotator. Specifically, an appropriate amount of a sealant coat material is placed on a substrate or stencil and the entire substrate or stencil is spun to produce a generally uniform sealant coat layer. In a preferred embodiment, the spin rate is between about 10 rotations per minute (rpm) and about 100,000 rpm. More preferably, the spin rate is about 500–20,000 rpm and, most preferably, is about 1,000–20,000 rpm. In order to make the coating thicker, multiple spin-deposition cycles can be used.

Alternatively, the sealant coat material can be deposited by spraying the sealant coat material onto a surface. For example, the sealant coat material can be ultrasonically sprayed through a nozzle or other orifice. In one embodiment, colloidal dispersions of the sealant coat material are prepared, the concentration being adjusted so that when sprayed onto a surface, a layer of desired thickness results. In another embodiment, the sealant coat material is sprayed directly onto a surface. In yet another embodiment, the sealant coat material is dissolved in an appropriate solvent and then sprayed onto the surface; when the solvent evaporates, the sealant coat material is left behind to form a coating layer. The sealant coat material can, alternatively, be applied by dipping a substrate and/or stencil into a volume of the sealant coat material. A single dip may produce a coating of desired thickness; in order to make the coating thicker, multiple dips may be applied. Alternatively, the sealant coat material can be deposited directly as a colloidal dispersion, or as a material dissolved in a solvent. In yet another preferred embodiment, the sealant coat material is stamped onto a surface. In all of these sealant deposition methods, the material may be further processed to ensure coating regularity or uniformity by methods such as pressing, rolling, scraping, and other equivalent methods known to those skilled in the art.

In another preferred embodiment, the material that is used to coat the surface of the microfluidic device is added to the device immediately prior to use, possibly after the device has already been constructed. For example, a coating material, such as a suspension or solvent containing solutes, particles, or beads, can be flushed through the microfluidic system immediately prior to use. Then further solvents and reactants may be added to the device to perform the desired synthesis. In a preferred embodiment, biological molecules can be flushed through the system immediately prior to use in order to prevent non-specific binding of molecules of interest such as proteins or nucleic acids. In another preferred embodiment, coating materials can be applied to the microfluidic system immediately prior to use that either promote or prevent cellular binding to surfaces. In this manner, cells can be localized within the microfluidic device where desired in order to perform cellular syntheses such as antibody production.

The embodiments described above are especially useful when the coating materials are damageable by light, air, or other environmental factors. For instance, certain coating materials may prove ineffective if exposed to oxygen or if they become dried out prior to use. Examples include, but are not limited to, collagen coatings used to promote cellular growth (which will be ineffective if dried prior to use). These coating materials would be difficult to store for extended periods of time without problematic packaging. Thus, it may be necessary to add these coating materials to a microfluidic device immediately prior to use, or within a reasonable amount of time prior to use. The period of time before use that a coating should be added depends on the particular coating selected.

In another preferred embodiment, the coating material can be applied using traditional vacuum deposition or lithography techniques as would be known by one skilled in the art. In one embodiment, coating materials are applied through vapor deposition, CVD, or electron deposition.

In a preferred embodiment of the present invention, the surfaces that form the microfluidic channels can be coated with molecules or materials that make the channel itself into a chromatography or affinity material. For instance, coatings can be applied that include specific chemical moieties on the surface of the coatings. The molecules in the solution will bind to the coating and remain there until the conditions are altered. Referring to FIG. 3A, the cross section of one portion of a microfluidic system is shown. In FIG. 3A, the chemical moieties are not drawn to scale. A microfluidic channel is composed of two stencil layers 600, 601 that compose a flow channel 602. The interior surfaces of the stencil layers 600, 601 that compose the channel 602 have been coated with chemical moieties. The coating can occur prior to the assembly of the device or after the assembly. In FIG. 3A, affinity binding molecules 603 have been attached to the surfaces of the stencils. For example, antibodies that specifically bind antigens can be covalently bound to the surface. Referring to FIG. 3B, when fluid is injected through the flow channel and the fluid contains a mixture of molecules 604, 605, molecules that are specific to the antibodies 603 on the surface, the molecules bind to the antibodies and are retained within the channel. The non-specific molecules 605 do not bind to the surface and are removed. In may be necessary to perform washing steps with differential stringency to remove unwanted molecules.

Another preferred embodiment is shown in FIG. 3C. In this embodiment, a microfluidic channel is composed of two stencil layers 610, 611, where the top surface of stencil 611 has been coated with a common chromatography material 612, —(CH2)17-CH3. This material 612 is commonly used for "reverse-phase" chromatography separations.

Other types of coatings may be used to perform a various separation techniques, as would be recognized by one skilled in the art. Such techniques include, for example: ion exchange, gel filtration or size exclusion, adsorption, partition, chromatofocusing, and affinity.

In a preferred embodiment, the sealant coat material is patterned (e.g., by printing methods including silk screening techniques) onto a surface. In this embodiment, the sealant coat material can be used to coat only certain selected areas of the surface as defined by the silk screening mask. In another preferred embodiment, photoresist patterning can be used to achieve liftoff or etch patterning. The photoresist can then be removed to leave a coating only on certain areas of the surface. This procedure can be repeated as desired or necessary using different photoresist patterns and coating materials. In alternate embodiments, a variety of thin film deposition techniques can be used to deposit sealant coat materials. Such techniques include, but are not limited to, thermal evaporation, e-beam evaporation, sputtering, chemical vapor deposition, and laser deposition. These and other thin film deposition techniques are well known in the art. In addition, plating techniques can be used to deposit sealant coat materials. Such plating techniques include, but are not limited to, electroplating of metallic materials and chemical plating. The thickness of the sealant coat may be important in certain embodiments. Preferably, the thickness of the coating is sufficient to chemically protect the underlying surface and/or to adhere or seal an adjacent substrate and/or stencil. A potential problem of too thick a coating is the obstruction or blockage of microstructures, which can impede or prevent fluid flow therein.

In certain embodiments, the coating materials serve to alter the local surface free energy of the device. This can alter the manner in which the fluid interacts with the surfaces of microfluidic channels and devices and thus alter their function. For instance, coating materials can serve to change the chemical nature of a microfluidic channel. In certain embodiments, coatings may be used to render selected portions of the device hydrophobic or hydrophilic. In other embodiments, coating materials that alter their ionic character depending upon the solvent and/or the pH may be used (for instance, a silane material that is terminated with a carboxylic acid, amino, or hydroxy group).

Where the sealant coat material does not solely serve an adherence function, thinner coatings can be used. In fact, a molecular layer (or monolayer) may be preferable in certain instances. In a preferred embodiment, the sealant coat is a self-assembled monolayer of alkane thiols, which is particularly amenable to deposition on metal surfaces such as gold. Other similar thiols can be used. In another preferred embodiment, silanization reactions can be used to coat the substrates. Silanization is known to minimize adherence of certain biological materials such as nucleic acids and peptides. In yet another preferred embodiment, the microstructures are coated with a lipid bilayer or multilayer. In certain embodiments, these molecular monolayers are terminated with a biological molecule that is used to bind a molecule in the solution. Examples include nucleic acid-terminated alkane thiols and protein-terminated silanes.

It is sometimes necessary to adjust the viscosity of the sealant coat material prior to the coating step. In order to obtain a desired viscosity, some of the sealant coat materials may need to be diluted or thinned with other solvents or chemicals. Alternatively, the sealant coat materials can be heated prior to their deposition to alter their viscosity. Appropriate viscosity adjustments will be apparent to those skilled in the art.

Substrates and stencils to be coated are preferably cleaned prior to the coating and adhesion steps. Examples of cleaning techniques include soaking, sonicating, rinsing and plasma cleaning. Examples of cleaning materials include soap, surfactants, detergents, organic solvents and Freon®.

In addition to coating surfaces, surfaces can be chemically modified by corona/plasma discharge or chemical treatment.

In another preferred embodiment, flexible sealant coat materials can be used on certain layers of the device in order to enable valving and pumping mechanisms. A preferred flexible sealant coat material is silicone rubber. Pressure or mechanical force can be applied to the flexible layer to cause the material to bend and block a channel located above or below it. Three-dimensional structures can be formed using stencils defining channels and/or chambers.

In certain embodiments, the sealant coat materials can be chemically bonded to the underlying substrate and to the next layer. Alternatively, non-covalent chemical interactions can be used to hold the substrates together. The stencil material can be melted onto the underlying substrate or adhered using an adhesive or some other mechanism, such as heating. In other embodiments, the stencil can be mechanically pressed onto the underlying or adjacent substrate.

In another preferred embodiment, the stencils are not used as the fluidic devices themselves, but rather they (or a portion thereof) are used as forms to define a positive or negative mold. Various molding materials can be used, such as moldable polycarbonate or various silicones (see, e.g., Duffy et al.). Microfluidic devices can be prepared comprising microstructures formed using such molds.

Fabrication methods not employing stencils at all may be used to fabricate microfluidic synthesis modules or devices according to the present invention. Conventional techniques including etching, molding, embossing, and/or micromachining may be employed. Circuit-board-type substrates may be used to fabricate microfluidic synthesis devices. Elements or modules fabricated according to the above-mentioned techniques may or may not be subsequently layered.

In certain embodiments, a secondary mechanism may be used to help seal substrates and/or stencils together. In certain embodiments, these layers are held together mechanically. Examples include using nuts and bolts, tight-fitting pegs and holes, epoxy, BLU-TEK®, or an external clamp. Alternatively, pressure or vacuum can be used to accomplish this mechanical adhesion or sealing.

In a preferred embodiment, a microstructure can be filled with any of a variety of filling materials, including column packing materials. In a preferred embodiment, the filling material is silica gel or a modified silica gel. In another preferred embodiment, the filling material is Sephadex® or Sephacil®. In a preferred embodiment, the filling material used to fill the channel and/or chamber is a biological material. Examples include, but are not limited to, binding proteins, antibodies, antigens, lectin, enzymes, lipids, and any molecules that may interact specifically or nonspecifically with one or more of the species in the fluid. In a preferred embodiment, filling materials are filters, which are useful for separating and/or purifying materials. These filters can be chemical or biological filters, or size-exclusion filters. These filters may bind unwanted material or, alternatively, may bind the material of interest so that it may be eluted off later. The filling materials can be hydrophobic or hydrophilic in nature, and can be charged or neutral. The filling material may be porous with various pore sizes. In a preferred embodiment, the filling material used to fill a channel or chamber is polymeric. Examples include, but are not limited to, polycarbonate, acrylic, polyurethane, high-density polyethylene (HDPE), ultra-high molecular weight polyethylene (UHMW), polypropylene (PP), polyvinylidene fluoride (PVDF), polytetrafluoroethylene (PTFE), Nafion®, nylon, and polyethersulfone (PES). In a preferred embodiment, the material used to fill the channel is a carbohydrate, such as agarose, alginate, starch, or carrageenan. In another preferred embodiment, the material used to fill the channel is acrylamide or agarose. In one preferred embodiment, the filling material is composed of a powder, such as charcoal or porous beads. In another preferred embodiment, the filling material is a paper filter. This filter may be a commercially available material that is chemically modified to perform a specific function, such as binding a material or filtering a variety of materials.

Various methods may be used to incorporate a filter into a microfluidic device. Filter configurations and materials may be selected to provide desired filtering utility. In certain applications, preventing leakage around the filter is not especially important. For these applications, a piece of filter material may be physically placed in a channel and suffice to collect or retain a limited percentage of desired material. Modifications can be made to prevent substantial leakage around the filter. The stencil layer comprising the channel surrounding the filter may be composed of a material that reflows under application of heat or pressure. In another example, an entire device layer may be fabricated from filter material, with apertures in adjacent layers to provide fluid access to the filter. In certain instances, lateral wicking of the fluid into the filter layer is problematic. To address this, at least one stencil layer (defining one or more apertures) adjacent to the filter layer may be selected to prevent substantial lateral wicking of the fluid into the filter layer. For example, the adjacent stencil layer may be a hot melt material that flows into the filter material at desired locations and further seals the filter. Other localized chemical or physical treatment of the filter may be performed to reduce lateral wicking.

In a preferred embodiment, the material is composed of a single component that is already formed prior to being placed into a microstructure. Alternatively, the material can be formed from multiple components that can be separately placed into a channel; once in the channel, the materials can react to form the final filling material. Such curing can be accomplished in a variety of ways, and can be spontaneous or catalyzed by some other mechanism such as light, heat, a catalyst, solvent, drying, etc.

In one embodiment, the filling material is placed into the microstructures during the manufacturing process. In this manner, high-throughput techniques can be used to fill the channels. In one embodiment, high-throughput pick-and-place equipment, like that used in the electronics industry, is used to place the filter materials. In one embodiment, the filling material is patterned into the microstructures by, for example, silk screening the material into the channels, or by using lithography, or by mechanically placing the material. In a preferred embodiment, an entire panel of devices can be coated simultaneously. A preferred panel size is approximately 18" by 24"; however, other panel sizes may be used. Fiducial marks may be placed on the panels for visual or optical alignment. Holes placed in the stencil may be used to align the stencil on the various machines used during the device manufacturing process. Silk screens comprising filter material may be are aligned with the devices on a panel.

In one embodiment providing filtering utility, a microfluidic filter is specially constructed to minimize leakage around the filter. Referring to FIGS. 5A–5B, a microfluidic device 50 is composed of five layers. Starting at the bottom of FIG. 5A, a first layer 51 supports a filter element 55 and defines an inlet port 56 and an outlet port 57. The second layer 52 is a stencil layer that defines a chamber 58 having larger lateral dimensions than the filter element 55, but the layer 52 has a thickness that is smaller than the height of the filter element 55. The second layer 52, which is preferably made from a polymeric material, further defines a channel and via 59 in fluid communication with the outlet port 57, and a via 60 in fluid communication with the inlet port 56. The third stencil layer 53, which is preferably also made of a flexible polymeric material, defines a third layer aperture 61 that is substantially centrally located atop the filter element 55 but is smaller in size than the filter element 55. Because the filter height is greater than the height of the second layer that forms the chamber, the third layer material above the filter is pressed tightly against the filter 55. The third layer 53 also defines a via 62. The fourth stencil layer 54, which may be made from a polymeric material, defines a channel 63 terminating at a fourth layer aperture 64 that is adjacent to, and preferably larger than, the third layer aperture 61. The channel 63 may also be enlarged at the inlet side to mate with the via 62 in the third layer 53. The assembled device 50 is shown in FIG. 5B, a portion of which (along section lines "A—A") is shown in sectional view in FIG. 5C. In operation, fluid enters the device 50 through the inlet port 56, through vias 60, 62 into the fourth layer channel 63 and into the fourth layer aperture 64. From the fourth layer aperture 64, fluid flows into the third layer aperture 61 and is then forced through the filter 55. The third layer aperture 61 essentially determines the functional area of the filter 55, and can be varied accordingly. Upon exiting the filter 55, fluid flows through the second layer aperture 59 to the outlet port 57. The configuration of the device 50 prevents leakage in two ways: the membrane 53 above the filter 55 is tight against it, and the fluid pressure that builds up to push fluid through the filter 55 also pushes the membrane 53 even tighter against the filter 55. While the particular filter and surrounding chamber illustrated in FIGS. 5A–5C are illustrated as circular in shape, other shapes may be used. In other words, the foregoing design is by no means limited to filter materials and chambers that are circular in shape.

Providing accurate measurement of stoichiometric microfluidic volumes of reagents and solvents is highly desirable to perform analyses on a microfluidic scale. FIGS. 6A–6B illustrate a microfluidic device 70 capable of sample metering and division. The microfluidic device 70 brings in a quantity of sample that has a large standard deviation, meters a known amount with a smaller standard deviation, divides the metered amount into three equal components, and brings the sample off-board for further analysis.

Referring to FIG. 6A, an inlet port 71, control port 72, and outlet ports 73 were created in a ⅛" thick polycarbonate base 87. Four stencil layers were created 74–77, each having channels 78–82 cut into them. In this example, single sided pieces of tape that consists of 3 mil (76-micron) polypropylene backing with permanent water based adhesive is used as the stencil material. The stencil layers were adhered together and onto the polycarbonate base. The assembled device is shown in FIG. 6B and contains four different types of overlap regions 83–86. All of the channels are 3-mils high, thus the overlap regions are 6-mils. At overlap 83, both channels are 40-mils wide and they overlap for 40-mils. At overlap 84, channel 80 is 40-mils wide and tapers down to 20-mils in the overlap region; channel 79 is 40-mils wide and channel 86 extends across 79 for 20-mils. Overlaps 85 and 86 are identical. The entry channels 79, 81 are 40-mils wide, the exit portions are 70-mils wide and the overlap is 40-mils in length.

In operation, a sample plug is injected at the inlet port 71 using a syringe pump at a constant flow rate. A fluidic impedance 83 is constructed immediately after the inlet to control the initial fluid flow. The fluid then passes into channel 79 and fills the channel until it reaches impedance 85. At this point, the excess fluid within the sample breaks through the microfluidic impedance at 84 before the microfluidic impedance at 85. The excess fluid passes down channel 80. Once all of the excess fluid has been sent to the waste channel 80, the control port 72 can be plugged, which increases the pressure within the channels. The amount of sample now ready for further analysis is defined by the volume of channel 79 between the two microfluidic impedances 84 and 85. If a different sample volume is desired, the microfluidic impedance 84 can be moved along channel 79 to alter the volume.

Once the air in channel 80 has been compressed sufficiently to build up enough pressure, microfluidic impedance 85 is overcome. The sample now enters chamber 81 and fills the entire chamber up to the impedances 86. Once this chamber has been completely filled, the output microfluidic impedances 86 are overcome and the samples can now be exported off the device for further analysis.

Providing regulation capability to usefully vary flow to particular regions in a microfluidic system is desirable in certain synthesis methods. Compensating a microfluidic system for changes in relative pressure is one application. One technique for controlling the sensitivity of a microfluidic system to changes in relative pressure is to change the area of a regulatory region by way of a deformable membrane. A microfluidic chamber may be separated from another microfluidic chamber using a deformable membrane. Specific membranes can come in a wide variety of geometries and shapes. Microfluidic channels or segments thereof can overlap in a perpendicular format, at a non-perpendicular angle, or along parallel portions.

Referring to FIGS. 7A–7D, in one embodiment a microfluidic regulation device 199 is formed in five layers. The first layer 200 serves as a cover; the second layer 201 defines a channel 205 having a circular regulatory region; the third layer is a flexible membrane defining two vias 208 in fluid communication with the channel 205; the fourth layer 203 defines a channel 206 leading to a circular chamber 207 and; the fifth layer 204 defines an inlet port 209, and two outlet ports 210, 211. In use, fluid enters the device at inlet port 209 and travels to channel 205. The fluid then travels to channel 206 where it is split into two streams leading to the exit ports 210, 211. As the channel 205 is pressurized to deform the membrane 202, the unrestrained portion of the membrane 202A will deform downward into the channel segment 207. Depending on various factors including the area of the membrane subject to deformation, the force applied, and material properties such as flexibility of the membrane, deformation of the membrane portion 202A towards channel segment 207 may result in substantially complete blockage of fluid flow between channel segments 207 and the port 210. Alternatively, the membrane portion 202A may be deformed so as only to reduce fluid flow between channel segment 207 and port 210. Referring to FIG. 7D, the unrestrained membrane portion 202A is deformed so as to partially block fluid flow between segment 207 and port 210. Devices according to this design can be constructed with the port 210 in various positions relative to the path of the deformable membrane 202A. By placing the port 210 in a position near to the center of travel of the deformable a membrane, a system can be constructed that can substantially block fluid flow through the through hole. The size and shape of the port will also affect the amount of pressure required.

In a preferred embodiment, the channel being controlled exits the regulatory region in a direction parallel to the direction of travel of the deformable membrane. Further material layers may be added to a flexible membrane regulation device, and the fluids on opposite sides of a membrane may be part of separate fluidic circuits. Referring to FIG. 7E, for example, a microfluidic regulation device is operated with a pressurized fluid, preferably air, contained in a first channel segment 225 adjacent to a flexible membrane layer 222. A rigid substrate 220 opposes the deformable membrane 222 along the first channel segment 225. A separate microfluidic circuit within the device permits fluidic passage between second and third channel segments 223, 227, which are connected with a hole 230 in an intermediary layer 224 adjacent to the unrestrained portion 222A of the flexible membrane. As the first channel 225 is pressurized, preferably with an external source (not shown), the deformable membrane portion 222A deforms downward to reduce the area of the second channel segment 227 adjacent to the hole 230, as shown in FIG. 7F. As the area of the second channel segment 227 is reduced, flow between the second and third channel segments 223, 227 is reduced. Further increases in pressure to the first channel segment 225 will completely block flow through the hole 230 within the device. The through hole 230 may be constructed in a variety of shapes to optimize regulation and/or shutoff characteristics. In different preferred embodiments, the through holes are circular and triangular in shape. Using this method, external control of flow (either regulation, shutoff or both) within a microfluidic device is provided.

Using these techniques, a system can be constructed in which deformation of the material results in either partial blockage or substantially complete blockage of the channel segment in response to a change in relative pressure. An elastic material can be used where reversible control of fluid flow is desired. Lowering the pressure in the higher relative pressure channel segment allows the deformable membrane to resume its neutral state, allowing unrestricted fluid flow. In some cases, it is desirable for the change in the microfluidic channel segment to be substantially permanent or irreversible. Such uses include shut-off valves to protect downstream components from damage caused by high flow or pressure. Upon increase in pressure in one channel segment, an inelastic material will be deformed towards the channel segment with lower pressure. The material will remain substantially in the deformed position.

A deformable membrane also can be made of materials with surface properties that alter its behavior. For example, a membrane can be tacky or have an adhesive coating. Such properties or coatings can be applied to one or both sides of the deformable membrane. Depending on the strength of the adhesive or degree of tackiness, the deformable membrane can operate as a variable switch. At low relative pressures, the membrane can act elastically. At high pressures, or for systems designed for the deformable membrane to physically contact the opposing wall of the adjacent channel segment, the deformation can result in a permanent closure of the adjacent channel segment. In another embodiment, the membrane used can be non-adhesive, but the surface against which it seals can be constructed with a tacky or adhesive surface. The degree of permanence of the closure relates to the elasticity of the membrane and the strength of the adhesive material used. Examples of the inelastic system include but are not limited to situations where the material is semi-malleable, for example, a metal foil, and situations where one or both of the surfaces have permanent or semi-permanent adhesives.

Mixing two or more fluidic streams is generally useful in performing synthesis efficiently. On a microfluidic scale, mixing fluidic streams is generally difficult since surface effects tend to be dominant. A method and apparatus for mixing two or more microfluidic streams is provided herein. In one embodiment, an aperture permitting the passage of one microfluidic stream is placed in contact with a microfluidic channel containing another microfluidic stream. Preferably, the aperture is at least as wide as the channel; more preferably, the aperture is further configured as a slit. Further preferably, the fluid supplied to the aperture travels in a direction parallel to the flow within the channel. Referring to FIGS. 8A–8B, a microfluidic mixing device 90 is constructed in five layers. FIG. 8A is an exploded view of the five layers, and FIG. 8B is a top view of the assembled device 90. The first layer 91 serves as a cover; the second layer 92 defines a microfluidic channel 94 terminating in a wide aperture 95; the third layer 96 defines a via 98 and a slit 99 positioned below the aperture 95 in the second layer 92; the fourth layer 100 defines a via 101 and a narrow microfluidic channel 102 that expands into wide microfluidic channel 103; and the fifth layer 104 defines two fluidic inlet ports 106, 107 and one fluidic outlet port 108. In operation, two different fluids are introduced to the device 90 through the inlet ports 106, 107. The first fluidic stream is quickly directed to the wide channel 103 in the fourth layer 100. The second fluidic stream passes upward to the second layer 92, and then downward through the aperture 95 and slit 99 into the wide channel 103 in the fourth layer 100. When the first and second fluid streams are present in the wide channel 103, the second fluid stream is initially layered atop the first fluid stream. Since the width of the channel 103 is much greater than its height, layering one fluidic stream atop the other provides a large contact area between the two streams to promote rapid diffusion. In practice, complete mixing between two streams is routinely observed within devices constructed according to FIGS. 8A–8B within channel lengths of 2 inches or less, depending on factors including fluid flow rates. As with the other microfluidic tools disclosed herein, the slit mixer 90 may be integrated with other components into complex microfluidic devices. Various materials may be used for the layers of the device 90.

Various microfluidic tools disclosed herein may be combined in complex microfluidic devices to perform analyses on a microfluidic scale. In one embodiment, microfluidic streams may be mixed in various proportions. For example, FIGS. 9A–9B illustrate a five-layer microfluidic device 110 according to an embodiment having two fluidic inlets, six unequal impedance branch channels for each fluid, six mixer overlap regions, and six filters. In this embodiment, the impedance of each channel is varied in a pre-determined ratio by varying the length of each channel with respect to the length of the other channels. Of course, similar impedance variation can be provided by otherwise varying the volume and/or geometry of the channel or by introducing impedance generated structures such as filters, porous layers or other like structures. FIG. 9A is an exploded view of the five layers, and FIG. 9B is a top view of the assembled device 110. Various materials may be used for the layers of the device 110. The first layer 111 serves as a cover. The second layer 112 defines a first supply channel 114 for directing a first fluid to six unequal-length branch channels 115. The supply channel 114 is significantly wider that the branches, preferably approximately equal to the sum of the widths of the branch channels 115. Each initially narrow branch channel 115 expands to a wider portion 116. The third layer 117 defines six mixer apertures 118 (configured as slits) at the end of each branch channel 116, six filter apertures 119, and a via 120. The fourth layer 121 defines a second supply channel 122 for directing a second fluid to six unequal-length branch channels 123. Each branch channel 123 terminates at widened portion positioned under a mixing aperture 118. The fourth layer 121 further defines six filter chambers 124 for holding filters 125, with each filter chamber 124 having a filter outlet channel 126. The six filter outlet channels 126 connect to a common outlet channel 128, which delivers fluid to outlet ports 131 in the fifth layer 129. The fifth layer 129 further defines inlet ports 130 for supplying fluids to the device 110. In operation, the device 110 receives two fluidic streams and splits each stream into six portions. For each stream, the flow rate of fluid leading to each of the six mixers is determined by the relative lengths of the channels leading to each mixer. Flow rate from a common supply is fastest to the shortest branch, and slowest to the longest branch (since the longest branch has a greater resistance to flow). Since the device 110 is configured to mix the contents of the shortest branch channel for the first fluid with the contents of the longest branch channel for the second fluid, and vice-versa, the resulting six mixtures each have different ratios of the first fluid to the second fluid. After mixing, the fluids are transported to individual filters 125. Preferably, the width of the outlet channels 126 is larger than the sum of the narrow branch channels 115, 123 to minimize flow resistance. In an alternative embodiment, the device may be constructed with in-layer filters downstream of the mixer overlap regions.

In a preferred embodiment of the invention providing thermal exchange utility, heating and/or cooling elements are used in conjunction with a microfluidic device. Such heating/cooling elements can be integrated into the microfluidic device or provided as external components that come into contact with the device. In a preferred embodiment, one portion of a heating device composes a portion of a microfluidic channel or chamber. Referring to FIG. 10A, a cross-section of a portion of microfluidic device is shown. The portion is composed of three stencil layers 500–502 and a heating element 503, which form a inlet/outlet channel regions 504 and a chamber 505. The top surface of the heating element 503 forms the bottom surface of the chamber 505. When the element 503 is heating, energy is transferred (by mechanisms including conduction and natural convection) into fluid occupying the chamber 505. In another preferred embodiment, the heating element is external to (i.e. not part of) the microfluidic device. Referring to FIG. 10B, a cross-section of a portion of microfluidic device is shown. The device portion is composed of three stencil layers 510–512, which form an inlet/outlet channel region 513 and a chamber 514. The top surface of a microfluidic heating element 515 is brought into contact with the microfluidic device. When the heating element 515 is activated, energy is conductively transferred through the bottom stencil layers 512 into the fluid occupying the chamber 514. The composition of stencil layer 512 can be tailored to optimize the thermal transfer rate between the heating element 515 and the chamber 514. In certain embodiments, stencil layers including layer 512 may be fabricated from metal to optimize thermal transfer. In other embodiments, thermally conductive polymers or other thermally conductive materials can be used. In certain embodiments, stencil layer 512 can be composed of materials that are poor thermal conductors in order to moderate the heat transfer. In other embodiments, the thickness of the stencil layer can be altered to change the thermal properties. In such an embodiment, a significant portion of the heat supplied by the element 515 may be conducted laterally, along the horizontal plane of stencil layer 512.

In another preferred embodiment of the current invention, an upper stencil layer 500 may also be composed of a thermally conductive material. A heat sink (not shown) may be added along the top surface of the device, above stencil layer 500. In this manner, utilizing a heater and/or heat sink, a thermal gradient can be generated within the microfluidic chamber 526.

In certain embodiments, it may be desirable to heat a microfluidic device in only a localized region. Referring to FIG. 10C, a cross-section of a portion of microfluidic device is shown. The portion is composed of five stencil layers 520–524, which form an inlet/outlet channel region 525 and a chamber 526. Stencil layer 524 is composed of a substantially thermally conductive material so as to maximize the thermal conduction between the top surface of the heating element 525 and fluid in the chamber 524. Stencil 522 is composed of a material which is substantially non-conductive promote the flow of energy into the chamber 526. In this embodiment, horizontal (lateral) heat transfer within the layers of the device is minimized.

In another preferred embodiment, a conducting material is placed within a microfluidic chamber so that voltage may be applied through the conducting material to resistively heat the conducting material, and thus the contents of the chamber. The size and composition of the conductive material can be adjusted so as to provide the desired level of resistive heating for a given application.

Heating and cooling elements useful within devices according to the present invention may come in various forms, including but not limited to electric heaters, thermoelectric heaters and coolers (Peltier devices), resistive heaters, capacitively coupled RF heaters, heat sinks, fluidic circuit heaters, heatpipes, chemical heaters, and other types.

In certain embodiments of the current invention, fluid within a microfluidic device is heated using an off-board heating mechanism. In some embodiments the heating mechanism does not come into physical contact with the microfluidic device. For example, electromagnetic radiation may be used to heat fluid within the device. In a preferred embodiment, the radiation is within the microwave spectrum. In another preferred embodiment, the radiation is within the infrared spectrum. Alternatively, an external heating mechanism may contact the device, including a sonic (preferably ultrasonic) heater used to induce heating of a fluid.

In a preferred embodiment, a microfluidic device is used to concentrate samples. The device is constructed so that the volume of the wide channel/chamber and the large hole is about 2–100,000 times larger than the remaining filter chamber and channel volume. A large sample can be injected and washed many times. Then, a very small volume of eluent can be added to remove the sample that had been adhered to the filter material in filter chamber 104. In an alternative embodiment, a microfluidic solid phase extractor utilizing a porous polymeric material may be provided. A sample is flowed through the porous polymeric material (which may be configured in various ways), causing the analyte to be absorbed by the porous material. A second solvent is then flowed through the polymeric material to extract the analyte.

In many embodiments, fabrication of three-dimensional microfluidic devices permits a large number of microfluidic components to be integrated into a small space. For example, in one embodiment a compact, three-dimensional splitting device for splitting a sample into a large number of aliquots is provided. Referring to FIGS. 11A–11B, a high-density splitting device 550 is constructed in seven layers, preferably from polymeric materials. The first layer 551 defines a central inlet port 558; the second layer 552 defines two crossing channels 559 intersecting under the inlet port 558; the third layer 553 defines four apertures 560 positioned under the distal ends of the crossing channels 559; the fourth layer 554 defines four crossing channels 561 centered below the apertures 560; the fifth layer 555 defines sixteen apertures 562 positioned under the distal ends of the crossing channels 561; the sixth layer 556 defines 16 crossing channels 563 centered below the apertures 562; the seventh layer defines 64 apertures 564 positioned under the distal ends of the crossing channels 563. In operation, a sample is injected into the central inlet port 558, and is split repeatedly to ultimately form 64 aliquots having approximately equal volumes. Outlet ports (not shown) may be provided in the seventh layer 557 to output the aliquots to another location within or without the device 550. The use of multiple layers to accomplish splitting creates a more precisely divided aliquots than are possible with two-dimensional splitting devices. A device 550 was constructed from square layers having side lengths of 2¼ inches, providing a splitter density 12.6 chambers/in$^2$, or 1.93 chambers/cm$^2$.

In an embodiment of the invention providing sampling utility, a microfluidic fraction collector is provided. The fraction collector permits a fluid to be sampled into discrete portions, each of which may be separately analyzed.

In a preferred embodiment, a microfluidic fraction collector is formed in multiple layers. Referring to FIGS. 12A–12B, five-layer microfluidic fraction collecting device 700 is illustrated. FIG. 12A provides an exploded view of the device 700, while FIG. 12B illustrates a top view of the assembled device 700. The first layer 701 is preferably a substrate and defines an inlet aperture 706 for a sample; the second layer 702 is preferably a double-sided tape material and defines a first inlet channel 707 connected to a first branch channel 708, and defines third and fifth branch channels 710, 712 not connected to the first inlet channel 707; the third layer 703 is preferably a film material and defines three outlet apertures 715 for the branch channels 708, 710, 712 and five impedance apertures 716 intended to restrict fluid flow between the second and fourth layers 702, 704; the fourth layer 704 is preferably a double-sided tape material and defines second and fourth branch channels 709, 711 and peripheral vias 717; the fifth layer 705 is preferably a film material and defines five outlet ports 718, corresponding to the five branch channels 708–712.

In operation, the outlet ports 718 are initially unobstructed. A sample is provided to the device 700 through the inlet port 706 and communicated through the first inlet channel 707 to fill the first branch channel 708 until the first outlet port 718 is obstructed, such as by placing adhesive tape (not shown) over the outlet port 718. Alternatively, a valve (not shown) may be placed at the outlet port 718. As pressure rises within the first branch channel, fluid flow overcomes the resistance of the corresponding impedance aperture 716 to flow into the second branch channel 709. Thereafter, fluid fills the second branch channel 709 until the corresponding outlet port is obstructed. In a like fashion, fluidic samples (fractions) are communicated sequentially to the third, fourth, and fifth branch channels 710, 711, 712. When the filling process is completed, all outlet ports 718 will be obstructed and all of the branch channels will contain fluidic samples. Fraction collectors providing similar utility may be constructed in other configurations.

Performing liquid chromatography in microfluidic volumes provides significant cost savings by reducing column packing materials, analytical and biological reagents, solvents, and waste. Small analyte requirements of microfluidic analytical devices are compatible with other microscale processes, such as organic synthesis. Microfluidic devices may also be made to be disposable. Embodiments using sandwiched stencil technology to fabricate the devices provide additional advantages, such as rapid and inexpensive prototyping and production, and the ability to use a wide range of materials for and within a device.

The quality of separation in chromatography depends heavily on the size of the injection plug, with a small and well-defined plug generally providing better results. The size of a sample plug within a microfluidic channel acting as a column may be varied by manipulating factors such as the packing material, packing density, and changing the position at which the sample is loaded onto the column. Disclosed herein is a method and apparatus for injecting a small plug of sample onto the microfluidic column. In a microfluidic device, an injection channel is adjacent to and preferably oriented perpendicular to a separation column. The injection channel is preferably adjacent to the separation column by being located in a layer adjacent to the layer in which the column is defined. There is little impedance to flow through the sample injection channel. Since the column is typically filled with a microporous material, however, there exists a significant impedance to flow into and through the separation column. Thus, the sample must be forced into the column so that a small, well-defined injection plug is formed. Further, injection of the sample is advantageously performed on the column (i.e. downstream of the front of the column) to prevent irregularities and manufacturing imperfections such as dead volumes at the front end of the column from broadening the injection plug.

Referring to FIG. 13, an exploded view of a five-layer microfluidic device for performing liquid chromatography according to one embodiment is shown. The first layer 1001 defines two inlet ports 1006 and two outlet ports 1008, along with waste ports 1007; the second layer 1002, which is preferably a hot melt adhesive layer, defines an injection channel 1010, an unloading channel 1011, and vias 1012; the third layer 1003 defines a straight channel 1013 for containing a packing material 1014; the fourth layer 1004 is preferably a hot melt adhesive layer; and the fifth layer 1005 is a substrate that is preferably rigid. In operation, the column packing 1014 is pre-wetted with a solvent delivered through the injection channel 1010. Then a sample is loaded onto the column 1014 via the injection channel 1010. Notably, the injection channel 1010 crosses the column 1014 on an adjacent layer and downstream of the beginning of the column 1014. The injection channel 1010 is positioned a sufficient distance downstream of the beginning of the column 1014 to avoid distortion or broadening of the injection plug. After the sample is pressurized to force sample onto the column 1014, the sample is purged from the injection channel 1010 with a mobile phase solvent. This solvent is then pressurized to elute the analytes. The analytes are then separated as they flow through the column packing 1014. The reverse process can be used to unload separated analytes from the column 1014. Again, imperfections at the end of the column are avoided with an unloading channel 1011 (having a fluidic impedance much lower than the separation column 1014) that crosses the column 1014 on an adjacent layer and upstream of the end of the column 1014.

A demonstration of on-column detection of two dyes was performed using a device 1000 according to the design of FIG. 13A. A red dye (acid red) and blue dye (fast green) were separated on the column 1014 and detected by visible absorbance spectrometry. Light was transmitted through the column 1014. The separation column 1014 was made by sealing a strip from a commercially available thin layer chromatography (TLC) plate into the device 1000. The stationary phase was silica gel, and the mobile phase was a 9:1 mixture of water and ethanol. Separation was successfully achieved, with results of the demonstration provided in FIGS. 14A–14B.

An additional advantage to the invention is that it is amenable to parallel processing separations. Multiple columns may be loaded using a single injection channel with little or no loss of sample. The entire injection channel can be filled with sample and then pressure can be applied to the channel to simultaneously inject the samples into each column.

Referring to FIGS. 15A–15B, a multi-column microfluidic liquid chromatography (LC) device 1020 was fabricated in eight layers 1021–1028 using a sandwiched stencil construction method. A laser cutter was used to cut and define various holes and channels in the layers of the device 1020. The first (cover) layer 1021, made of 10-mil polyester film, included injection ports 1029 and column outlet ports 1030. The second layer 1022 was a 5.8 mil double-sided tape with a polyester carrier and rubber adhesive to adhere to the first and third layers 1021, 1023. The second layer 1022 included an injection channel 1031 having a segment perpendicular to the columns 1038 (placed into the fifth layer 1025), and vias 1032 connecting to the column outlet ports 1032. Both the third and fourth layers 1023, 1024 included injection vias 1033, 1034 and outlet vias 1035, 1036 in the same configuration. The second layer 1022 was a 0.8 mil polyester film, and the third, fourth, sixth, and seventh layers 1023, 1024, 1026, 1027 were made from 4-mil modified polyolefin thermoplastic adhesive. Alternatively, a thicker thermoplastic adhesive layer, if available, could be substituted for the third and fourth layers 1023, 1024 (and likewise for the sixth and seventh layers 1026, 1027) to provide enough thermoplastic material to seal any gaps around the columns 1038. The fifth layer 1025 was made of a 10-mil polyester film from which several channels 1037, each 40-mils wide, were removed. 40-mil width strips 1038 of polyester coated with silica gel, approximately 17 mils thick including a 250 µm coating thickness (Whatman Cat. No. 4410 221) were placed into the respective channels 1037 to serve as liquid chromatography column packing. The eighth layer 1028 was a rigid substrate. Gaps around the LC columns 1038 were sealed to prevent leakage by laminating the thermoplastic layers (the fourth, sixth, and seventh layers 1023, 1024, 1026, 1027) around the fifth layer 1025 using a conventional pouch laminating machine. Following assembly of all the layers, the device 1020 was re-laminated to ensure that any spaces around the columns 1038 were filled. Notably, while only three columns 1038 are illustrated in the device 1020, other embodiments according to similar designs may be easily constructed with a multitude of columns, without any loss of performance.

In operation, the two ports 1029 to the injection channel 1031 on the device 1020 were connected to syringes 1040, 1041 and valves 1042, 1043 via flexible tubing 1044 as shown in FIG. 16. Pressures were applied to the solutions by placing weights (not shown) above the syringes 1040, 1041. The first syringe 1040 contained water and the second syringe 1041 contained an aqueous solution of acid red (red) and fast green (blue) dyes. The first valve 1042 was initially closed and the second valve 1043 was initially open. The column packing 1038 was first wetted with water by increasing the water pressure to 5 psi. The states of the two valves 1042, 1043 were then reversed, to cause the first valve 1042 to open and the second valve 1043 to close. The injection channel 1031 was filled with dye solution by pressurizing the second syringe 1041. The dye solution was not allowed to flow into the first syringe 1040. A pressure of 5 psi was applied to both syringes 1040, 1041 to force dye into the three chromatography columns 1038. The states of the two valves 1042, 1043 were reversed again and water was flushed through the injection channel 1031 to a waste container 1044. The second valve 1043 was then closed, and the first syringe 1040 (containing water) was pressurized to approximately 5 psi to propel the dye plugs through the columns 1038. After the dye plugs were separated on the three columns 1038, the water in the first syringe 1040 was replaced with ethanol. The second valve 1043 was opened and the injection channel 1031 was then flushed with ethanol by pressurizing the first syringe. The second valve 1043 was then closed and the first syringe 1040 was pressurized to approximately 5 psi to deliver ethanol until both dyes had eluted from the columns 1038.

Any removal of a narrow plug of analyte from a column is susceptible to broadening and consequent ruining of the separation. Thus it is advantageous to be able to detect separated analytes on the column before they encounter these plug-broadening components. The chromatography device described here is highly amenable to on-column optical detection. As shown schematically in FIG. 17, for example, a device 1050 can be constructed of low-absorbance polymers so that light can pass through the polymer films 1051, 1053 and column 1052. Holes, such as hole 1055, can be incorporated into one or more opaque supporting layers (e.g., layer 1054) adjacent to optically clear layers 1051, 1053 that enclose the column. Alternatively, a hole (not shown) may be defined in a layer (e.g., layer 1051) enclosing the column 1052 and covered with a window of appropriate optical properties. Using a light source 1056, light can be transmitted through one or more windows, or reflected back through a window after interacting with an analyte on the column. A detector 1057, which may be within or preferably outside the device 1050, is preferably provided. These configurations enable a range of optical spectroscopies including absorbance, fluorescence, Raman scattering, polarimetry, circular dicroism and refractive index detection. With the appropriate window material and optical geometry, techniques such as surface plasmon resonance and attenuated total reflectance can be performed. These techniques can also be performed off-column as well or in a microfluidic device that does not employ a separation column. Window materials can also be used for other analytical techniques such as scintillation, chemilluminescence, electroluminescence, and electron capture. A range of electromagnetic energies can be used including ultraviolet, visible, near infrared and infrared.

Analytical probes (not shown) can also be inserted into the microfluidic device and into the separation column. Examples of optical probes include absorbance, reflectance, attenuated total reflectance, fluorescence, Raman, and optical sensors. Other probes and sensors include wide ranges of electrochemical and biochemical probes.

In a preferred embodiment of this invention, electrodes are placed in the channels and/or chambers. As examples of various electrode configurations, wires may be placed between stencil layers so as to protrude into channels, wires may be propagated within channels, or stencil layers may be fabricated from conductive foils. Additionally, stencil layers may be patterned with metallic film. In further embodiments, current can be passed through conductive elements disposed in a microstructure to induce heating within the microstructure. Thermocouples can be constructed within the microstructure using the conductive elements to detect thermal changes. Calorimetry can be performed in this manner. In addition, a magnetic field can be induced in a similar manner. This magnetic field can be used to detect certain phenomena or induce flow using magnetic particles.

A number of materials can be used as stationary phase for liquid chromatography. Examples include, but are not limited to, powders of silica gel and silica gel coated with a chemical group such as an 18-carbon alkane. Functional powders have particle diameters typically ranging from 3 to 10 micrometers for high performance liquid chromatography, but can be hundreds of micrometers in diameter for low pressure liquid chromatographies. Incorporating the particles, often termed "packing," into a chromatography column is difficult using conventional techniques. Using a slurry of particles in a fluid or a suspension of particles in a gas are typical methods of packing a column. Typically, a filter material known as a packing frit must be painstakingly inserted into the downstream end before the packing and to the upstream end after the packing.

One embodiment of the invention described herein provides a much simpler packing method in that the particles are packed before lamination of microfluidic layers. In one method, the particles are pressed into an open channel just prior to lamination of one or more adjacent layers. The particles can be applied as a dry powder or slightly wetted with a fluid. An inert binder may be added to the fluid so that upon drying, the particles will be immobilized in the channel, thus avoiding the need for packing frits. A liner can be used to keep the particles away from the sealing surface of the layer. If used, the liner is removed prior to lamination of the device. In another embodiment, the particles are deposited with an inert binder onto a sheet, as is common in thin layer chromatography.

In open channel chromatography, stationary phase material is applied only to the inner walls of a capillary column by passing a dilute solution of the coating material through the capillary. This and similar methods can be applied to a microfluidic device after the device has been assembled. A simpler method entails coating a film of material with the stationary phase. The coated film can then be used as the upper and lower layers of a microfluidic assembly with the coated side of the film forming two edges of the column.

As discussed previously, small injection plugs are necessary for achieving a separation. Performing injection in a cross-column configuration allows a small injection plug to be formed. The size of the injection plug can be further reduced after it is on the column by splitting the plug between the column and a waste outlet. A microfluidic LC device may be operated in different ways to accomplish this splitting. For example, FIGS. 18A–18F provide schematic cross-sectional views of a multi-layer microfluidic separation device 1060 and various operational methods to split an injection plug 1060 between a column 1065 and a waste outlet 1067. FIG. 18A illustrates the injection of a sample plug 1068 from an injection channel 1066. In FIG. 18B, a stream of solvent is provided to the column 1065 by the injection channel 1066. Since resistance to flow is greater along the length of the column than in the direction of the waste outlet 1067, the majority of the solvent stream flows toward the waste outlet 1067, carrying a large portion 1068A of the injection plug. A small remaining portion 1068B of the injection plug is carried by solvent and elutes down the column. After the plug 1068 has been split, a valve in the injection channel (not shown) can be closed to prevent further flow into the waste channel 1067. A second method is provided in FIGS. 18C–18D. After a sample plug 1068 is delivered to the column by the injection channel, solvent is provided to the column 1065 through the waste channel 1067. As solvent is added, a large portion 1068A of the plug flows into the injection channel 1066, and a smaller portion 1068B remains in the column 1065 for separation. A third method is provided in FIGS. 18E–18F. The spacing between the "waste" channel 1067 and the "injection" channel 1066 is reduced to provide a smaller plug. First, a sample plug 1068 is delivered to the column 1065 by the "waste" channel 1067. As the "injection" channel 1066 is maintained at a relatively low pressure, a large portion 1068A of the plug flows into the "injection" channel 1066 and a small portion 1068B remains in the column 1065. Solvent is provided to the column 1065 through the "waste" channel 1067, eluting the small portion 1068B for separation in the column 1065.

According to one embodiment of the invention, a microfluidic analytical device provides both separation and detection capabilities. A schematic diagram of one embodiment of the present invention is shown in FIG. 19. This flow diagram describes a general analytical technique for the current invention. As would be appreciated by one skilled in the art, variations on this theme are possible as certain individual steps may be rearranged or omitted for particular applications. Referring to FIG. 19, two inlet ports 481, 482 provide solvent to two regulators 483, 484 that feed a mixing device 485. Downstream of the mixer 485 is a separation chamber 486. A sample inlet port 480 delivers sample to the device between the mixer 485 and the separation chamber 486. Alternatively, the sample may be injected within the separation chamber 486. In a further alternative embodiment, sample may be injected using one of the solvent inlets 481, 482. In another embodiment, the solvent may be mixed "off-board," necessitating only one solvent inlet. More solvent inlets can be added to increase the complexity of the solvent mixture.

The mixing region 485 effectively mixes the solvent before it reaches the separation chamber 486. The separation chamber 485 can be configured in a variety of ways, as would be recognized by one skilled in the art, to perform techniques such as ion exchange, gel filtration or size exclusion, adsorption, partition, chromatofocusing, and affinity chromatographies. In one embodiment, the separation chamber 486 is a straight channel filled with stationary phase material. The length of the channel may be varied as needed to perform the desired separation.

The exit of the separation chamber 486 leads to the initial flow-through detector 487. Preferably, detection is provided off the device. Alternatively, on-board detection may be provided. The flow-through detection scheme will typically be set up so that molecules or atoms of interest can be detected while the fluid is still flowing. Examples of the flow-through detectors 487 include but are not limited to UV-visible spectroscopy, Raman spectroscopy, fluorescence detection, chemiluminescence, electrochemical detection, and other electronic detections such as capacitive and conductivity measurement.

Typically, the flow-through detector 487 will be used to pre-screen the fluid as it comes off the separation chamber 486 to determine if the given fluid has molecules of interest for further analysis or storage. In FIG. 19, a flow-through detector 487 leads to a diverter module 488 which can direct the fluid to a waste chamber 489, a secondary detector module 490, or a fraction collector 491. The fraction collector 491 contains an additional diverter 492 and a number of collection chambers 493–495. More or less collection chambers may be used.

Typically, the secondary detector 490 will be a destructive detection technology such as mass spectrometry, nuclear magnetic resonance, evaporative light scattering, ion mobility spectrometry, or immobilization on material such as glycerol or porous silicon for MALDI (matrix assisted laser desorption ionization). It may be necessary for the detector 490 to have an off-board collection mechanism, such as collection into a vial, capillary tube, hose, etc. that leads to the detector 490. Alternatively, a sampling mechanism can be built into the microfluidic device so that the sample is directly injected into an off-board detection system. For example, the outlet of the diverter 488 can lead to an open port to be used for electrospray.

In a preferred embodiment of the present invention, a parallel processing microfluidic analytical device is constructed. The term "parallel processing" as used herein refers to multiple microfluidic systems on a given contiguous device wherein some or all of the systems are in fluid communication with one another. In a preferred embodiment, multiple fluidic inlets are provided to a parallel processing microfluidic device. In another embodiment, multiple fluid inlets, outlets, and/or detectors are in communication with more than one microfluidic system on a given device. In these embodiments, a variety of simultaneous analytical processes may be accomplished using a small number of control inputs or outputs.

In a preferred embodiment, a plurality of analytical separation chambers or channels are on a single microfluidic device. This plurality of separation chambers are connected to microfluidic inlet ports that are used to insert samples for separation. The inlet ports for sample injection and solvent injection can be the same ports or different ports. In a preferred embodiment of the invention, the plurality of separation chambers are connected in such a way that a single sample injection port may deliver fluid to a plurality of separation chambers. In this manner, sample can be injected at a single macroscopic connection but be loaded onto a multitude of chambers.

In one embodiment, a multitude of separation chambers can be connected to a small number of solvent inlets that simultaneously or serially apply solvent in known mixtures to said separation chambers. In this manner, a small number of "off-board" pumps can be used to control a multitude of separation chambers.

In another embodiment of the current invention, the microfluidic separation chambers are connected to a network of microfluidic channels that lead to a smaller number of detection systems. The microfluidic channels can have a variety of valves, regulators, and other tools incorporated in a device in order to direct the fluids to the detection systems in a sequential manner. Alternatively, the outlet channels may direct the fluid from the separation chambers to the detection portions simultaneously. In this manner, a small number of detection systems can be used to detect molecules off a larger number of separation chambers.

Referring to FIG. 20, a schematic illustrating a parallel processing microfluidic analysis system according to one embodiment is shown. The system has inlet ports 510, 511 that are connected to splitters 512, 513. Each splitter is connected to two regulators 514–517 for individually regulating the pressure and/or flow of solvent to each of the mixers 518, 519. In a preferred embodiment, the regulators are externally controlled (such as provided in FIGS. 7E–7F) so that the user can specify the mixing ratios of fluids A and B when they reach the mixers 518, 519. In another preferred embodiment, the regulators are fixed so that a known constant mixing ratio will be achieved at the outlet of each mixer module. In FIG. 20, a sample inlet is not illustrated, but one or more inlets can be provided in various locations. In one embodiment, a sample is injected to both separation chambers 520, 521. In another embodiment, multiple samples are injected. The mixers 518, 519 lead to two separation chambers 520, 521. The separation media can be composed of a variety of components or single components. Each separation chamber has an individual flow-through detector 522, 523. The flow-through detectors may be of various types. In embodiment, off-board detectors that scan from one channel to the other are used. Very fast scanning can be accomplished with appropriate optics, as will be recognized by one skilled in the art. Alternatively, both channels 522, 523 can be probed simultaneously. This probing can be accomplished by various methods such as scanning or splitting a single light source, or by providing multiple light sources or other detectors. In a preferred embodiment, a non-invasive detection technology (such as UV-visible absorption) using off-board components is used to probe the fluid immediately past the separation chambers 520, 521. Then, if a molecule of interest is detected using the off-board detector, the diverters 524, 525 may send the fluid to a secondary detector 527 (possibly using destructive methods). Alternatively, if no signal of interest is detected, then the sample may be diverted to a waste chamber 526. Other components such as a fraction collector could be added.

The embodiment shown in FIG. 20 would allow two pumps to control the solvents for two systems. To accomplish the same result in a non-parallel processing manner, four pumps would be required. While it is possible to provide and operate multiple parallel systems on a device, as the number of systems increases, it becomes problematic to increase the number of inlet ports, pumps, and detectors at the same rate. In many applications, these off-board systems are be expensive and large. Thus, if it is desired to simultaneously perform 100 separations, a parallel device would require 200 inlet ports, 200 pumping systems, 100 waste chambers and 100 detectors. It is therefore illustrated that parallel processing enables simplified implementation of multiple analyses on a single microfluidic device.

In embodiments described above, a multitude of separation chambers can be added by simply increasing the number of on-board regulators, splitters, mixers, and diverters. These on-board devices can be built into the chip and be microfluidic in nature, if desirable in a particular application. In this manner, the number of inlet ports and off-board pumps and detectors remains constant.

While microfluidic tools and devices provided herein have been applied to perform analyses, they may also be combined and/or integrated with further tools to perform syntheses. Modular or integrated microfluidic devices having regions for performing syntheses and analyses are contemplated.

It is to be understood that the illustrations and descriptions of views of individual microfluidic tools, devices and methods provided herein are intended to disclose components that may be combined in a working device. Various arrangements and combinations of individual tools, devices, and methods provided herein are contemplated, depending on the requirements of the particular application. The particular microfluidic tools, devices, and methods illustrated and described herein are provided by way of example only, and are not intended to limit the scope of the invention.

What is claimed is:

1. A microfluidic device for passively mixing at least two fluids for analysis, the device comprising a plurality of device layers defining:

a first fluidic input;

a first junction or manifold region in fluid communication with the first fluidic input;

a first plurality of unequal impedance branch channels in fluid communication with the first junction or manifold region;

a second fluidic input;

a second junction or manifold region in fluid communication with the second fluidic input;

a second plurality of unequal impedance branch channels in fluid communication with the second junction or manifold region;

a plurality of mixer regions in fluid communication with the first plurality of unequal impedance branch channels and the second plurality of unequal impedance branch channels, wherein the plurality of mixer regions, the first plurality of unequal impedance branch channels, and the second plurality of unequal impedance branch channels are disposed within the plurality of device layers so as to permit simultaneous and combination of a first fluid and a second fluid in a plurality of different predetermined mixing ratios; and a detection region in fluid communication with the plurality of mixer regions.

2. The microfluidic device of claim 1 wherein:

the impedances of the branch channels first plurality of unequal impedance branch channels vary in a first predetermined impedance ratio from a first higher impedance channel to a first lower impedance channel;

the impedances of the branch channels second plurality of unequal impedance branch channels vary in a second predetermined impedance ratio from a second higher impedance channel to a second lower impedance channel;

the first higher impedance channel is in fluid communication with the second lower impedance channel; and the second higher impedance channel is in fluid communication with the first lower impedance channel.

3. The microfluidic device of claim 2 wherein:

the branch channels of the first plurality of unequal impedance branch channels each have a length proportional to the first predetermined impedance ratio; and the branch channels of the second plurality of unequal impedance branch channels each have a length proportional to the second predetermined impedance ratio.

4. The microfluidic device of claim 1 further comprising a plurality of porous regions associated with the first plurality of unequal impedance branch channels and the second plurality of unequal impedance branch channels.

5. The microfluidic device of claim 1 wherein the plurality of device layers includes at least one porous layer associated with the first plurality of unequal impedance branch channels and the second plurality of unequal impedance branch channels.

6. The microfluidic device of claim 1 wherein the plurality of device layers further defines a plurality of overlap regions associated with the plurality of mixer regions.

7. The microfluidic device of claim 1 wherein the plurality of device layers further defines a plurality of slit regions associated with the plurality of mixer regions.

8. The microfluidic device of claim 1 further comprising a plurality of filters associated with the detection region.

9. The microfluidic device of claim 1 wherein any device layer of the plurality of device layers is fabricated with a polymeric material.

10. The microfluidic device of claim 1 wherein any device layer of the plurality of device layers is fabricated with an adhesive tape material.

11. The microfluidic device of claim 1 wherein any device layer of the plurality of device layers is a stencil layer.

12. The microfluidic device of claim 1 wherein the detection region is substantially optically transmissive.

13. The microfluidic device of claim 1 wherein at least one device layer of the plurality of device layers is fabricated with a substantially optically transmissive material.

14. The microfluidic device of claim 1 wherein the detection region is adapted to interface with an analytical tool that performs an analytical technique selected from the group consisting of: UV-visible spectroscopy, Raman spectroscopy, fluorescence detection, chemiluminescence, electrochemical detection, capacitive measurement, and conductivity measurement.

* * * * *